US012611507B2

(12) United States Patent \
Eilertsen et al.

(10) Patent No.: US 12,611,507 B2 \
(45) Date of Patent: Apr. 28, 2026

(54) DRUG DELIVERY DEVICE, SUBASSEMBLY FOR DRUG DELIVERY DEVICE, SYRINGE HOLDER, AND METHOD OF ASSEMBLY

(71) Applicant: AMGEN INC., Thousand Oaks, CA (US)

(72) Inventors: Lars Eilertsen, Søborg (DK); Troels Pedersen, Gilleleje (DK); Kasper Hjortkjaer Nielsen, Copenhagen V (DK); Jacob Lykke Jensen, Copenhagen S (DK); Peter Werner Hansen, Birkerod (DK)

(73) Assignee: AMGEN INC., Thousand Oaks, CA (US)

( * ) Notice: Subject to any disclaimer, the term of this patent is extended or adjusted under 35 U.S.C. 154(b) by 863 days.

(21) Appl. No.: 17/690,035

(22) Filed: Mar. 9, 2022

(65) Prior Publication Data

US 2022/0288326 A1     Sep. 15, 2022

Related U.S. Application Data

(60) Provisional application No. 63/159,356, filed on Mar. 10, 2021.

(51) Int. Cl.
*A61M 5/20*        (2006.01)
*A61M 5/32*        (2006.01)

(52) U.S. Cl.
CPC ........ *A61M 5/2033* (2013.01); *A61M 5/3204* (2013.01); *A61M 2005/2013* (2013.01);
(Continued)

(58) Field of Classification Search
CPC .......... A61M 5/2033; A61M 2005/206; A61M 5/3202; A61M 5/20; A61M 5/326;
(Continued)

(56) References Cited

U.S. PATENT DOCUMENTS 5,681,291 A     10/1997 Galli \
8,647,299 B2    2/2014 Stamp \
(Continued)

FOREIGN PATENT DOCUMENTS

CN     110215571 A     9/2019 \
CN     112188908 A     1/2021 \
(Continued)

OTHER PUBLICATIONS

International Application No. PCT/US2022/019416, International Search Report and Written Opinion, mailed Jul. 13, 2022.
(Continued)

*Primary Examiner* — Wesley G Harris

(57) ABSTRACT

A syringe holder for a drug delivery device is provided. The syringe holder may include a proximal end, a distal end, and a hollow interior configured to receive at least a portion of a syringe. The syringe holder may further include a side opening distal to the proximal end and an outwardly extending protrusion proximal to the side opening. During assembly of the syringe holder into a housing of the drug delivery device the outwardly extending protrusion may be configured to support the syringe holder at a first axial position or an intermediate position with respect to a longitudinal axis of the housing of the drug delivery device. Also provided is a drug delivery device incorporating a syringe holder and a subassembly for a drug delivery device incorporating a syringe holder. A method of assembling a syringe holder into a housing of a drug delivery device is also provided.

20 Claims, 15 Drawing Sheets

(52) U.S. Cl.

CPC ............... *A61M 2005/3247* (2013.01); *A61M 2005/3267* (2013.01); *A61M 2207/00* (2013.01)

(58) Field of Classification Search

CPC ............ A61M 2207/00; A61M 5/3157; A61M 2005/3247; A61M 2005/2013; A61M 2005/3267; A61M 5/3204; A61M 5/3243; A61M 5/24

See application file for complete search history.

(56) References Cited

U.S. PATENT DOCUMENTS

| | | | |
|---|---|---|---|
| 8,932,254 B2 | 1/2015 | Eaton | |
| 8,992,476 B2 | 3/2015 | Shang et al. | |
| 10,137,248 B2 | 11/2018 | Holmqvist et al. | |
| 10,556,068 B2 | 2/2020 | Glover et al. | |
| 10,569,019 B2 | 2/2020 | Hirschel et al. | |
| 10,583,255 B2 | 3/2020 | Maxfield | |
| 10,918,803 B2 | 2/2021 | Kemp et al. | |
| 11,027,068 B2 | 6/2021 | Mosebach et al. | |
| 11,318,252 B2 | 5/2022 | Zhang | |
| 11,376,363 B2 | 7/2022 | Alexandersson | |
| 11,607,494 B2 | 3/2023 | Hirschel et al. | |
| 11,648,348 B2 | 5/2023 | Alexandersson | |
| 11,850,400 B2 | 12/2023 | Holmqvist et al. | |
| 2010/0152655 A1 * | 6/2010 | Stamp ..................... | A61M 5/24 604/196 |
| 2012/0053528 A1 | 3/2012 | Bollenbach et al. | |
| 2017/0106146 A1 * | 4/2017 | Folk ........................ | A61M 5/20 |
| 2018/0140782 A1 * | 5/2018 | Kemp ................. | A61M 5/2033 |
| 2019/0060579 A1 * | 2/2019 | Daniel .................... | A61M 5/20 |
| 2019/0217022 A1 | 7/2019 | Gentz et al. | |
| 2020/0030536 A1 | 1/2020 | Lannan et al. | |
| 2020/0268970 A1 | 8/2020 | Holmqvist et al. | |
| 2020/0397993 A1 | 12/2020 | Stamp | |

| | | | | |
|---|---|---|---|---|
| 2021/0077743 A1 | | 3/2021 | Kemp et al. | |
| 2021/0228807 A1 | | 7/2021 | Holmqvist et al. | |
| 2021/0353862 A1 | | 11/2021 | Schrul et al. | |
| 2022/0008661 A1 | | 1/2022 | Kemp | |
| 2022/0362470 A1 | | 11/2022 | Alexandersson | |

FOREIGN PATENT DOCUMENTS

| | | | | | |
|---|---|---|---|---|---|
| EP | 1532997 A1 | * | 5/2005 | ............ | A61M 5/326 |
| EP | 2758102 B1 | | 8/2015 | | |
| EP | 2788055 B1 | | 2/2017 | | |
| EP | 3153196 A1 | | 4/2017 | | |
| EP | 2781230 B1 | | 8/2019 | | |
| EP | 3695863 A1 | * | 8/2020 | ......... | A61M 5/3202 |
| EP | 2739329 B2 | | 9/2020 | | |
| EP | 1998831 B1 | | 10/2020 | | |
| EP | 3811991 A1 | | 4/2021 | | |
| WO | WO-9504565 A1 | * | 2/1995 | ........ | A61M 25/0631 |
| WO | 1999022792 A1 | | 5/1999 | | |
| WO | WO-2007109352 A2 | * | 9/2007 | ............ | A61M 5/326 |
| WO | WO-2010146358 A2 | * | 12/2010 | ......... | A61M 5/2033 |
| WO | WO-2011145999 A1 | * | 11/2011 | ......... | A61M 5/2033 |
| WO | 2014146210 A1 | | 9/2014 | | |
| WO | WO-2016152958 A1 | * | 9/2016 | ............... | A61J 1/16 |
| WO | 2016193341 A1 | | 12/2016 | | |
| WO | 2016193374 A1 | | 12/2016 | | |
| WO | WO-2016202555 A1 | * | 12/2016 | ......... | A61M 5/2033 |
| WO | WO-2017029032 A1 | * | 2/2017 | ......... | A61M 5/2033 |
| WO | 2018167491 A1 | | 9/2018 | | |
| WO | 2020/037256 A1 | | 2/2020 | | |

OTHER PUBLICATIONS

Office Action received in Eurasian Patent Application No. 202392533, dated Oct. 20, 2023.

First Examination Report received in counterpart Saudi Arabia Patent Application No. 523450625, dated Oct. 27, 2024.

* cited by examiner

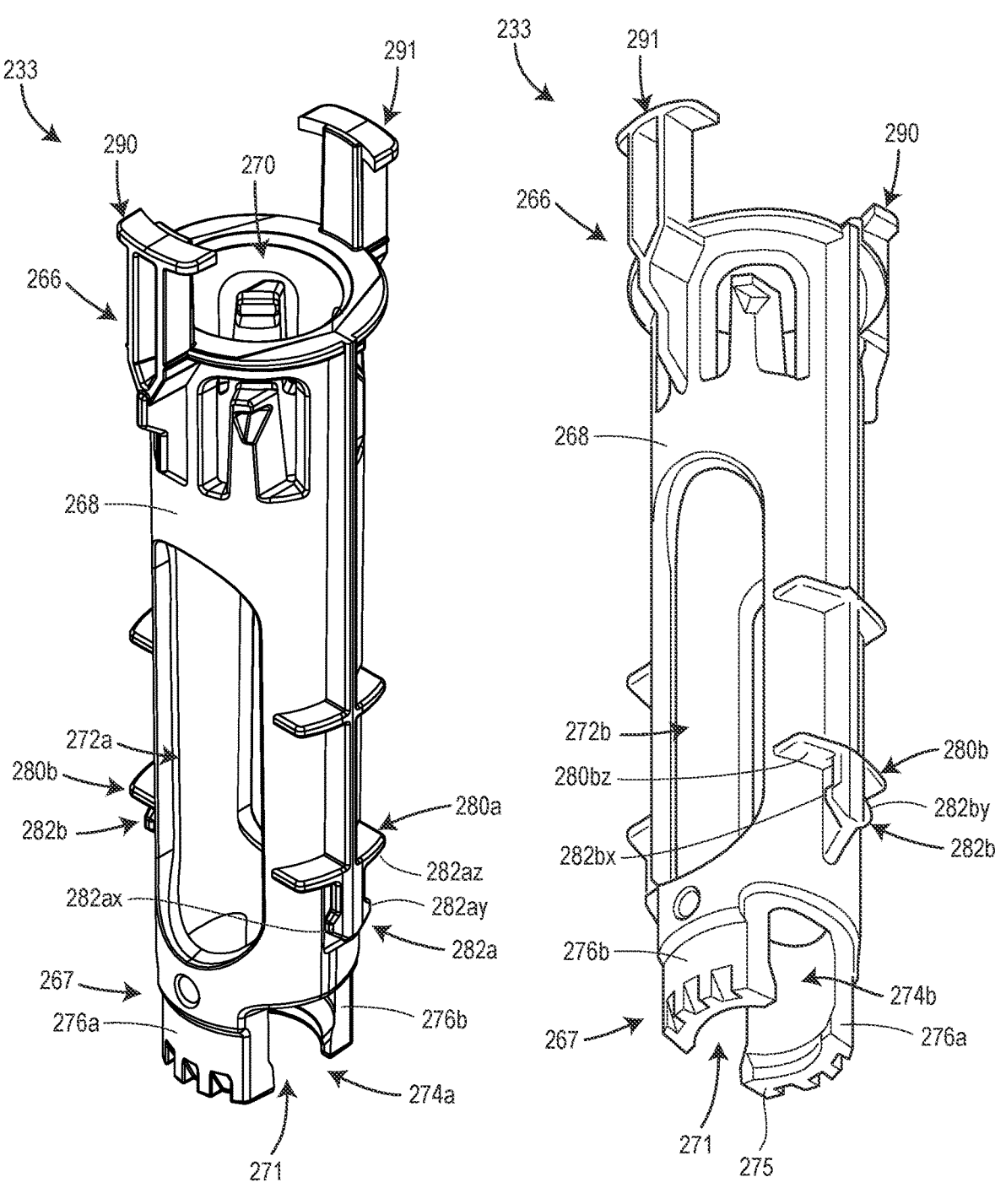
FIG. 16                    FIG. 17

DRUG DELIVERY DEVICE, SUBASSEMBLY FOR DRUG DELIVERY DEVICE, SYRINGE HOLDER, AND METHOD OF ASSEMBLY

CROSS-REFERENCE TO RELATED APPLICATION

Priority is claimed to U.S. Provisional Patent Application No. 63/159,356, filed Mar. 10, 2021, the entire contents of which are hereby expressly incorporated by reference herein.

FIELD OF DISCLOSURE

The present disclosure generally relates to drug delivery devices and, more particularly, devices for automatically injecting a drug into a patient and the manufacture of such devices.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional forms of drug delivery including, for example, delivery via a conventional syringe.

Many drug delivery devices include a housing and a syringe stored within the housing. During the manufacture of such devices, it may be necessary or desirable to inspect the syringe and/or a syringe holder used to mount the syringe within the housing. After the syringe and/or syringe holder are assembled into the housing, inspecting the syringe and/or the syringe holder may not be feasible because a wall of the housing may block them from view. Certain housings include a window designed to allow a user to view a portion of the syringe before, during, and/or after operation of the drug delivery device. However, such windows typically reveal only a limited portion of the syringe and, as a result, may not allow one to inspect certain portions of the syringe and/or syringe holder inside the housing.

The present disclosure sets forth drug delivery devices embodying advantageous alternatives to existing drug delivery devices, subassemblies for drug delivery devices, syringe holders for drug delivery devices, and related methods of assembly, and that may address one or more of the challenges or needs mentioned herein.

SUMMARY

One aspect of the present disclosure provides a syringe holder for a drug delivery device. The syringe holder may include a proximal end, a distal end, and a hollow interior configured to receive at least a portion of a syringe. The syringe holder may further include a side opening distal to the proximal end and an outwardly extending protrusion proximal to the side opening. During assembly of the syringe holder into a housing of the drug delivery device, the outwardly extending protrusion may be configured to support the syringe holder at a first axial position or an intermediate position with respect to a longitudinal axis of the housing of the drug delivery device.

The outwardly extending protrusion may be configured to contact a first inner portion of the housing of the drug delivery device when the syringe holder is in a first rotational position with respect to the housing of the drug delivery device to prevent the syringe holder from moving in a distal direction with respect to the housing of the drug delivery device. The outwardly extending protrusion may be configured to permit movement of the syringe holder in a proximal direction with respect to the housing of the drug delivery device when the syringe holder is in the first axial position. The outwardly extending protrusion may be configured such that the outwardly extending protrusion is rotationally offset from the first inner portion of the housing of the drug delivery device when the syringe holder is in a second rotational position with respect to the housing of the drug delivery device to permit movement of the syringe holder in the distal direction with respect to the housing of the drug delivery device. At least a portion of the syringe holder may be configured to contact a second inner portion of the housing of the drug delivery device when the syringe holder is in a second axial position or a final assembled position with respect to the longitudinal axis of the housing of the drug delivery device to prevent the syringe holder from moving in the distal direction with respect to the housing of the drug delivery device.

Another aspect of the present disclosure provides a subassembly for a drug delivery device. The subassembly may include a syringe holder and a housing. The syringe holder may include an outwardly extending protrusion. The housing may include a hollow interior configured to receive at least a portion of the syringe holder, a first inwardly extending protrusion, and a second inwardly extending protrusion distal to the first inwardly extending protrusion. During assembly, the syringe holder may be arranged in a first axial position with respect to a longitudinal axis of the housing where the outwardly extending protrusion of the syringe holder contacts the first inwardly extending protrusion of the housing and arranged in a second axial position with respect to the longitudinal axis of the housing where at least a portion of the syringe holder contacts the second inwardly extending protrusion of the housing.

A further aspect of the present disclosure provides a drug delivery device comprising including a housing having an opening and a syringe including a needle having an insertion end configured to extend at least partially through the opening during a delivery state. The drug delivery device may further include a syringe holder as described generally above.

An additional aspect of the present disclosure provides a method of assembling a syringe holder into a housing of a drug delivery device. The method may include arranging the syringe holder at least partially within the housing of the drug delivery device at a first axial position with respect to a longitudinal axis of the housing of the drug delivery device. The method may further include, while the syringe holder is arranged in the first axial position within the housing of the drug delivery device, inserting a syringe into the syringe holder. Additionally, the method may include moving the syringe holder and the syringe in a distal direction with respect to the longitudinal axis of the housing of the drug delivery device to a second axial position within the housing of the drug delivery device.

Arranging the syringe holder at the first axial position within the housing of the drug delivery device may include coupling the syringe holder to the housing of the drug delivery device to prevent the syringe from moving in at least the distal direction with respect to the housing of the drug delivery device. Arranging the syringe holder at the first axial position within the housing of the drug delivery device may include coupling the syringe holder to the housing of the drug delivery device to prevent the syringe from rotating with respect to the housing of the drug delivery device. Prior to moving the syringe holder and the syringe to the second axial position within the housing of the drug delivery device, the method may include decoupling the syringe holder from the housing of the drug delivery device. Decoupling the syringe holder from the housing of the drug delivery device may include moving syringe holder in a proximal direction with respect to the housing of the drug delivery device and/or rotating the syringe holder with respect to the housing of the drug delivery device from a first rotational position to a second rotational position. Decoupling the syringe holder from the housing may include moving the syringe holder in a proximal direction with respect to the housing of the drug delivery device prior to rotating the syringe holder from the first rotational position to the second rotational position.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIGS. 11-13 illustrate the syringe holder in a first axial position and a first rotational position. FIG. 14 illustrates the syringe holder in a second rotational position. FIG. 15 illustrates the syringe holder in a second axial position and the second rotational position.

FIG. 16 is a perspective view of an exemplary syringe holder in accordance with various embodiments.

FIG. 17 is a perspective view of the syringe holder of FIG. 16.

FIG. 18 is another perspective view of the syringe holder of FIG. 16.

FIG. 19 is an enlarged view of a portion of the syringe holder of FIG. 16.

DETAILED DESCRIPTION

The present disclosure generally relates to drug delivery devices operable by a user for administering a drug, or in a scenario where the user is a patient, self-administering a drug, as well as subassemblies and components for drug delivery devices and methods of assembling drug delivery devices. A drug delivery device or a subassembly thereof according to the present disclosure may include a syringe holder and a housing having a hollow interior configured to receive the syringe holder. The syringe holder may be mounted at different axial positions within the housing during different stages of an assembly sequence. For example, the syringe holder initially may be mounted at a first axial position within the housing, and, then, later in the assembly sequence, may be mounted at a second axial position within the housing. The first axial position may facilitate the ability of a manufacturer to inspect a syringe inserted into the syringe holder, the syringe holder itself, and/or other aspects of the drug delivery device while the syringe and/or the syringe holder are contained within the housing. The second axial position may correspond to, for example, a final assembled position of the syringe holder and syringe within the housing. The ability to inspect the syringe and/or syringe holder when the syringe holder is in the first axial position may allow one to, for example, check if the syringe has been properly secured within the syringe holder, check a drug contained inside in the syringe for particulates and/or contaminants, and/or check a wall of the syringe for fractures and/or other damage, among other safety checks. Furthermore, the ability to inspect the syringe and/or syringe holder after they have been inserted into the housing of the drug delivery device may facilitate manufacturing efficiencies and/or bring flexibility to the manufacturing process, for example, by providing a manufacturer with greater freedom with respect to when and/or where the inspection process is performed and/or freeing the manufacturer from having to assemble the syringe into the syringe holder outside of the housing and then inspect those components while they are outside of the housing. These and other advantages will be apparent to one of ordinary skill in the art reviewing the present disclosure.

Figure 1:
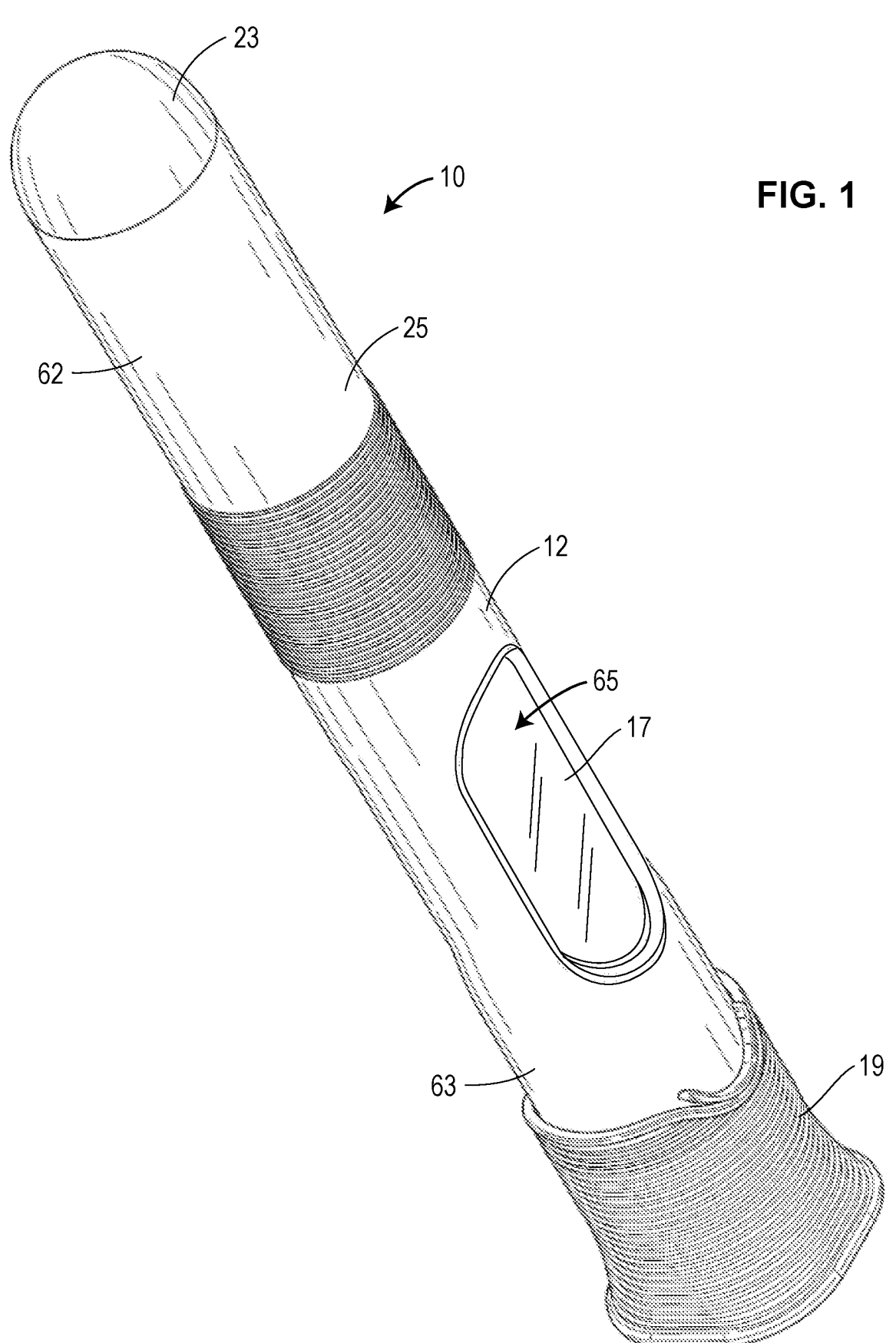
FIG. 1 is a perspective view of an exemplary drug delivery device in accordance with various embodiments.
Figure 2:
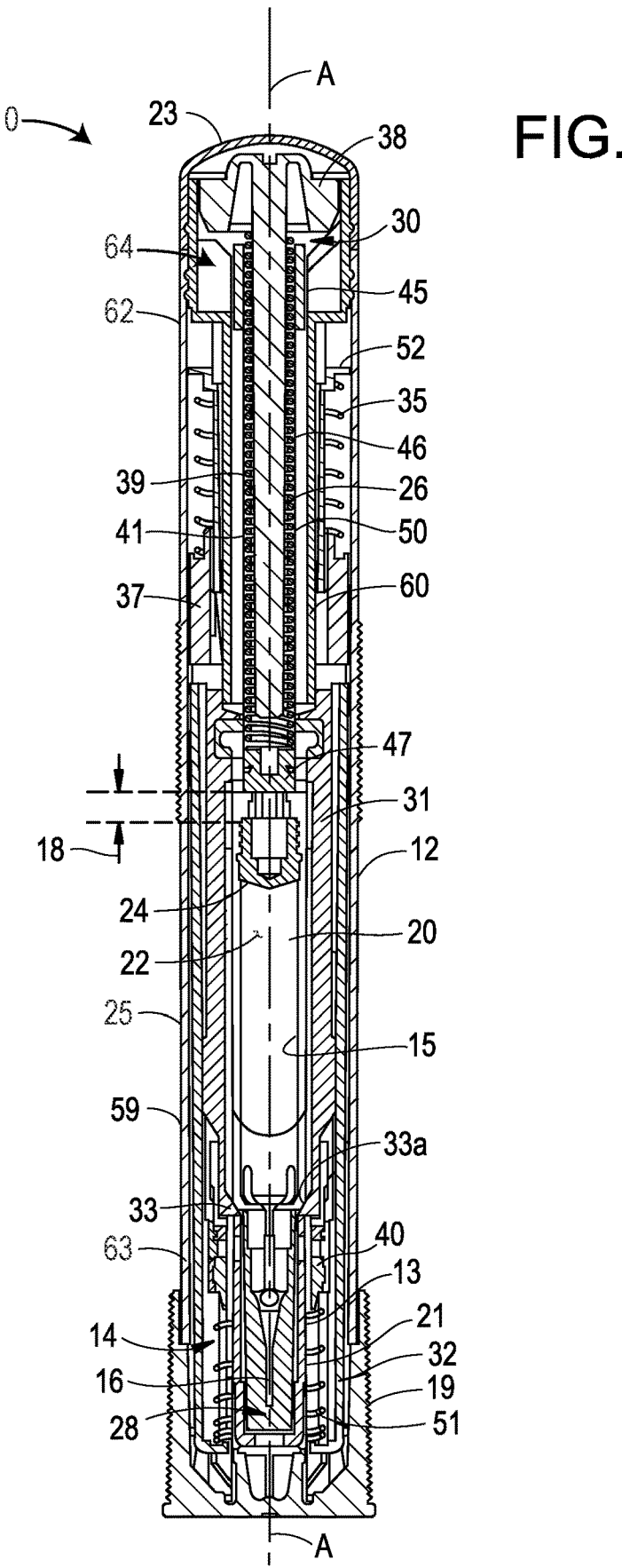
FIG. 2 is cross-sectional view of the drug delivery device of FIG. 1.

FIGS. 1 and 2 illustrate several views of an embodiment of a drug delivery device 10 for delivering a drug, which may also be referred to herein as a medicament or drug product. The drug may be, but is not limited to, various biologics such as peptides, peptibodies, or antibodies. The drug may be in a fluid or liquid form, although the present disclosure is not limited to a particular state. The drug delivery device 10 illustrated in FIGS. 1 and 2 may be in its final assembled form and/or in a storage state prior to operation by a user.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by caregiver or a formally trained healthcare provider (e.g., a doctor or nurse). The exemplary the drug delivery devices shown in the Figures may take the form of an autoinjector or pen-type injector, and, as such, may be held in the hand of the user over the duration of drug delivery, but may also or alternatively be suitable for other drug delivery devices and/or configurations.

The configuration of various components included in the drug delivery device 10 may depend on the operational state of the drug delivery device 10. The drug delivery device 10 may have a storage state, a pre-delivery state, a delivery or dosing state, and a post-delivery state, although fewer or more states are also possible. For example, each state may have several sub-states or stages. The storage state may correspond to the configuration of the drug delivery device 10 in FIGS. 1 and 2, where the delivery device includes a removable cap in a storage position. In some embodiments, the storage state may exist in the time between when the drug delivery device 10 leaves a manufacturing facility and when a patient or other user removes the removable cap. The pre-delivery stage may correspond to the configuration of the drug delivery device 10 after the removable cap has been removed but prior to activation of a drive mechanism by the user. This may include the moments in time after the user has removed the removable cap, while the user is first positioning the drug delivery device 10 against the injection site, but before dosing has begun. The delivery state may correspond to the configuration of the drug delivery device 10 while drug delivery, also referred to herein as dosing, is in progress. The post-delivery state may correspond to the configuration of the drug delivery device 10 after drug delivery is complete and/or when a stopper is arranged in an end-of-dose position in a drug storage container.

With continued reference to FIGS. 1 and 2, the drug delivery device 10 includes an outer casing or housing 12. In some embodiments, the housing 12 may be sized and dimensioned to enable a person to grasp the injector 10 in a single hand. The housing 12 may have a hollow, generally elongate shape, such as a cylindrical shape, and extend along a longitudinal axis A between a proximal end 62 and a distal end 63. As an example, the housing 12 may include a wall 25 having a generally annular shape (e.g., a tubular shape) and defining a hollow interior (e.g., an interior space or cavity) of the housing 12. As a more specific example, the wall 25 may surround and/or be centered about the longitudinal axis A.

An axial opening 14 (FIG. 2) may be formed in the distal end 63 of the housing 12 to permit an insertion end 28 of a delivery member 16 to extend outside of the housing 12. An axial opening 64 may formed in the proximal end 62 and may be covered partially or entirely with an end cap 23 when the drug delivery device is in its final assembled form. The end cap 23 may have a generally hemispherical shape or any other suitable shape. A side opening 65 may be formed in the wall 25 of the housing 12 and may be covered partially or entirely by a transparent or semi-transparent inspection window 17. The window 17 may permit a user, manufacturer, and/or other individual or a machine to view component(s) inside the drug delivery device 10, including a drug storage container 20. Viewing the drug storage container 20 through the window 17 may allow a user to confirm that drug delivery is in progress and/or complete and/or check the drug for color discoloration, cloudiness, and/or other visual characteristics. A removable cap 19 may cover the axial opening 14 at the distal end 63 of the drug delivery device 10 prior to use of the drug delivery device 10, and, in some embodiments, may include a gripper 13 (FIG. 2) configured to assist with removing a removable sterile barrier 21 (e.g., a rigid needle shield (RNS), a non-rigid needle shield (nRNS), etc.) mounted on the insertion end 28 of the delivery member 16. The gripper 13 may include one or more inwardly protruding barbs or arms that frictionally or otherwise mechanically engage the removable sterile barrier 21 to pull the removable sterile barrier 21 with the removable cap 19 when the user separates the removable cap 19 from the housing 12. Thus, removing the removable cap 19 has the effect of removing the removable sterile barrier 21 from the delivery member 16.

In some embodiments, the housing 12 may be constructed in one-piece, such that the housing 12 is defined by a single, monolithic structure. In other embodiments, the housing 12 may be constructed of multiple, interconnected structures.

The drug storage container 20 may be disposed within the hollow interior of the housing 12 and may be configured to contain a drug 22. The drug storage container 20 may be pre-filled with the drug 22 and shipped, e.g., by a manufacturer, to a location where the drug storage container 20 is combined with a remainder of the drug delivery device 10. For example, the drug 22 may be distributed and/or provided to patients in more than one use case, such as a as a pre-filled syringe or as an autoinjector including a pre-filled syringe. By utilizing the same or similar syringe components in either case, at least some of above steps such as filling, labeling, packaging, shipping, and distribution may be streamlined or simplified for two different use cases. As another example, in the event that multiple use cases utilize some or all of the same syringe components, some regulatory pathways to marketing and/or distributing the drug may be streamlined and/or simplified for at least one of the multiple use cases.

The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between proximal end and a distal end of the drug storage container 20. The stopper 24 may be constructed of rubber or any other suitable material. The stopper 24 may slidably and sealingly contact an interior surface 15 of the wall of the drug storage container 20 such that the drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap 18. Upon activation of a drive mechanism 30 of the drug delivery device 10, the plunger 26 moves in the distal direction to close the gap 18 and comes into contact with the stopper 24. Subsequent distal movement of the plunger 26 drives the stopper 24 in the distal direction to expel the drug 22 from the drug storage container 20. In alternative embodiments, the stopper 24 and the plunger 26 may initially be in contact with one another or coupled to one another, e.g., via a threaded coupling, such that they move together jointly from the start of movement of the plunger 26. Once the stopper 24 is in motion, it may continue to move in the distal direction until it contacts a proximally directed portion of the interior surface 15 of the wall of the drug storage container 20. This position of the stopper 24 may be referred to as the end-of-dose or end-of-delivery position, and may correspond to when delivery of the drug 22 to the patient is complete or substantially complete.

In some embodiments, a volume of the drug 22 included in the reservoir of the drug storage container 20 may be equal to 1 mL, or equal to approximately (e.g., ±10%) 1 mL, or equal to 2.5 mL, or equal to approximately (e.g., ±10%) 2.5 mL, or equal to 3 mL, or equal to approximately (e.g., ±10%) 3 mL, or less than or equal to approximately (e.g., ±10%) 1 mL, or less than or equal to approximately (e.g., ±10%) 2 mL, or less than or equal to approximately (e.g., ±10%) 3 mL, or less than or equal to approximately (e.g., ±10%) 4 mL, or less than approximately (e.g., ±10%) 5 mL, or less than or equal to approximately (e.g., ±10%) 10 mL, or within a range between approximately (e.g., ±10%) 1-10 mL, or within a range between approximately (e.g., ±10%) 1-5 mL, or within a range between approximately (e.g., ±10%) 1-4 mL, or within a range between approximately (e.g., ±10%) 1-3 mL, or within a range between approximately (e.g., ±10%) 1-2.5 mL.

The delivery member 16 is connected or operable to be connected in fluid communication with the reservoir of the drug storage container 20. A distal end of the delivery member 16 may define the insertion end 28 of the delivery member 16. The insertion end 28 may include a sharpened tip of other pointed geometry allowing the insertion end 28 to pierce the patient's skin and subcutaneous tissue during insertion of the delivery member 16. The delivery member 16 may be hollow and have an interior passageway. One or more openings may be formed in the insertion end 28 to allow drug to flow out of the delivery member 16 into the patient.

In some embodiments, including the embodiment illustrated in FIG. 2, the drug storage container 20 may be a pre-filled syringe having a staked, hollow metal needle for the delivery member 16. Here, the needle is fixed relative to the wall of the drug storage container 20 and may be in permanent fluid communication with the reservoir of the drug storage container 20. In other embodiments, the needle may be coupled to the drug storage container 20 via a Luer Lock or other suitable connection. In yet other embodiments, the drug storage container 20 may be a needle-less cartridge, and, as such, initially may not be in fluid communication with the delivery member 16. In such embodiments, the drug storage container 20 may move toward a proximal end of the delivery member 16, or vice versa, during operation of the drug delivery device 10 such that the proximal end of the delivery member 16 penetrates through a septum covering an opening in the drug storage container 20 thereby establishing fluid communication between the reservoir of the drug storage container 20 and the delivery member 16.

As described below in more detail, the drug delivery device 10 may also include a container holder 33 configured to, for example, secure the drug storage container 20 with respect to the housing 12, such as by preventing distal movement of the drug storage container 20 with respect to the housing 12 during actuation of the plunger 26 during the delivery state and/or during transportation and/or handling during the storage state and/or pre-delivery state. The container holder 33 may be referred to herein as a syringe holder in embodiments where the drug storage container 20 is a syringe.

The drug delivery device 10 may further include a guard mechanism for preventing contact with the insertion end 28 of the delivery member 16 when the drug delivery device 10 is not being used to administer an injection. The guard mechanism may include a guard member 32 moveably disposed at the distal end of the housing 12 adjacent to the opening 14. The guard member 32 may have a hollow and generally cylindrical or tubular shape centered generally about the longitudinal axis A, and may have a proximal end received within the housing 12. The guard member 32 may be configured to move relative to the housing 12 between an extended position wherein a distal end of the guard member 32 extends through the opening 14 in the housing 12 and a retracted position wherein the distal end of the guard member 32 is retracted, fully or partially, into the opening 14 in the housing 12. Additionally or alternatively, the guard member 32 may be configured to move from the retracted position to the extended position. When moving from the extended position to the retracted position, the guard member 32 may translate linearly in the proximal direction; and when moving from the retracted position to the extended position, the guard member 32 may translate linearly in the distal direction. In at least the extended position, the guard member 32 may extend beyond and surround the insertion end 28 of the delivery member 16. In embodiments where the delivery member 16 protrudes from the opening 14 in the housing 12 in the pre-delivery or storage state, moving the guard member 32 from the extended position to the retracted position, e.g., by pressing the distal end of the guard member 32 against the patient's skin at the injection site, may result in the insertion end 28 of the delivery member 16 being inserted into the patient's skin.

The guard mechanism may further include a guard biasing member 35 and a guard extension 37. The guard extension 37 may be positioned proximal to the guard member 32; and the guard biasing member 35 may be positioned proximal to the guard extension 37. The guard extension 37 may have a hollow and generally cylindrical or tubular shape centered about the longitudinal axis A. Furthermore, the guard extension 37 may be moveable in a linear direction along the longitudinal axis A relative to the housing 12. In the present embodiment, the guard extension 37 is a separate structure from the guard member 32. However, in alternative embodiments, the guard extension 37 and the guard member 32 may be integrally formed in one piece to define a single, monolithic structure. In such alternative embodiments, the proximal end of the guard member 32 may correspond to the guard extension 37.

The guard biasing member 35 may be positioned between and in contact with the guard extension 37 and a releaser member 52. The guard biasing member 35 may be configured to bias or urge the guard extension 37 in the distal direction and bias or urge the releaser member 52 in the proximal direction. The guard biasing member 35 may initially be in an energized (e.g., compressed) state such that it exerts a biasing force on the guard extension 37 and a biasing force on the releaser member 52 in the pre-delivery state. In some embodiments, a distal end of the guard extension 37 is initially in contact with a proximal end of the guard member 32, as seen in FIG. 2. As a consequence, the guard extension 37 transfers a biasing force of the guard biasing member 35 to the guard member 32, such that the guard biasing member 35 biases or urges the guard member 32 toward the extended position. A user may overcome the biasing force by pressing the guard member 32 against the injection site. In doing so, the guard member 32 and the guard extension 37 move jointly in the proximal direction until, for example, the guard member 32 reaches the retracted position. When the injection is complete and the drug delivery device 10 is lifted off of the injection site, the guard biasing member 35 may push the guard extension 37 so that the guard extension 37 and the guard member 32 move jointly in the distal direction. This motion returns the guard member 32 to the extended position, which has the effect of covering the insertion end 28 of the deliver member 16. In some embodiments, the guard biasing member 35 may include a compression spring (e.g., a helical compression spring). Furthermore, in embodiments where the plunger biasing member 50 also includes a compression spring, the guard biasing member 35 may disposed around and/or have a larger diameter than the plunger biasing member 50.

After drug delivery is complete and the guard member 32 has been re-deployed to the extended position, it may be desirable to lock the guard member 32 in the extended position to prevent subsequent user contact with the insertion end 28 of the delivery member 16 and/or to prevent re-use of the drug delivery device 10. Pursuant to these ends, some embodiments of the drug delivery device 10 may include a lock ring 40 configured to selectively rotate, depending on the axial position of the guard member 32, in order to lock the guard member 32 in the extended position once the guard member 32 has moved from the retracted position to the extended position. In the present embodiment, the lock ring 40 is centered and rotates about the longitudinal axis A. As illustrated in FIG. 2, a proximal end of the lock ring 40 may be in contact with the container holder 33 and the distal end of the lock ring 40 may be disposed at least partially within the guard member 32. The lock ring biasing member 51 may be positioned in the axial direction between a distally facing surface of the lock ring 40 and a proximally facing surface of the guard member 32. The lock ring biasing member 51 may initially be in a compressed or energized state such that it biases the lock ring 40 and the guard member 32 away from each other. As such, the lock ring biasing member 51 may exert a biasing force urging the guard member 32 toward the extended position, as well as exert a biasing force urging the proximal end of the lock ring 40 against the container holder 33. In some embodiments, the lock ring biasing member 51 may include a compression spring (e.g., a helical compression spring). In some embodiments, rotation of the lock ring 40 may be achieved by a camming arrangement between the lock ring 40 and the container holder 33.

The drug delivery device 10 may further include a drive mechanism 30 disposed partially or entirely within the housing 12. Generally, the drive mechanism 30 may be configured to store energy and, upon or in response to activation of the drive mechanism 30 by the user, release or output that energy to drive the plunger 26 to expel the drug 22 from the drug storage container 20 through the delivery member 16 into the patient. In the present embodiment, the drive mechanism 30 is configured to store mechanical potential energy; however, alternative embodiments of the drive mechanism 30 may be configured differently, for example, with the drive mechanism 30 storing electrical or chemical potential energy. Generally, upon activation of the drive mechanism 30, the drive mechanism 30 may convert the potential energy into kinetic energy for moving the plunger 26.

In the present embodiment, the drive mechanism 30 includes the plunger biasing member 50, a plunger biasing member seat 38, the releaser member 52, and a plunger guide 60. The plunger biasing member 50 may include a compression spring (e.g., a helical compression spring) which is initially retained in an energized state. In the energized state, the plunger biasing member 50 may be compressed such that its axial length is shorter than it would be in a natural or de-energized state. When released, the plunger biasing member 50 may try to expand to its natural axial length, and as a consequence, exert a biasing force pushing the plunger 26 in the distal direction.

The plunger biasing member 50 may be disposed at least partially within the plunger 26, and may have a distal end abutting against a proximally facing inner surface of the plunger 26 and/or may be fixedly attached to an inner surface of the plunger 26. So that the plunger biasing member 50 may be received within the plunger 26, an outer diameter or other dimension of the plunger biasing member 50 may be equal to or less than an inner diameter of the a ring 45 and/or equal to or less than an inner diameter of the hollow rod 46. In some embodiments, the distal end of the plunger biasing member 50 may abut against a proximally facing inner surface of the base 47 of the plunger 26. Furthermore, a proximal end of the plunger biasing member 50 may abut against a distally facing surface of the plunger biasing member seat 38. The plunger biasing member seat 38 may be fixedly attached to the tubular housing 25 such that the plunger biasing member seat 38 provides a stationary surface for the plunger biasing member 50 to push off of. So configured, the plunger biasing member 50, when released from the energized state, may expand in length with distal end of the plunger biasing member 50 moving in the distal direction away from the stationary proximal end of the plunger biasing member 50. This motion may push the plunger 26 is the distal direction, which, in turn, may push the stopper 24 in the distal direction to expel the drug 22 from the drug storage container 20 into the delivery member 16 and thereafter into the patient.

The releaser member 52 may have a hollow and generally cylindrical or tubular shape, and may be centered about the longitudinal axis A. As illustrated in FIG. 2, the releaser member 52 may be positioned in the radial direction between the distal end of the plunger guide 60 and a proximal end of the guard extension 37. Furthermore, the releaser member 52 may be arranged radially inwardly of the guard biasing member 35. Generally, the releaser member 52 is configured to operably couple the guard member 32 and the plunger 26 in an activation sequence and to generate an audible signal indicating the end of drug delivery. So configured, the releaser member 52 is exploited to perform two separate functions, and thus reduces the number of moving parts required by the drug delivery device 10.

The releaser member 52 may be configured to rotate relative to the housing 12 and/or translate linearly relative to the housing 12, depending on the stage of operation of the drug delivery device 10. Initial rotation of the releaser member 52 associated with activation may be powered by the plunger biasing member 50 and/or the guard biasing member 35; whereas later rotation of the releaser member 52 associated with generation of the end-of-dose signal may be powered solely by the guard biasing member 35. Any linear translation of the releaser member 52 without rotation may be powered solely by the guard biasing member 35. In some embodiments, the releaser member 52 may translate linearly only in the proximal direction; however, alternative embodiments may permit linear translation of the releaser member 52 in both the proximal and distal directions.

An ability of the releaser member 52 to rotate about the longitudinal axis A may be regulated by an interaction between an outer portion of an annular wall of the releaser member 52 and an inner portion of the guard extension 37. The guard extension 37 may be prevented from rotating about the longitudinal axis A as a consequence of its coupling to the housing 12. This has the effect of preventing rotation of the releaser member 52 about the longitudinal axis A when abutment structures (e.g., outwardly extending projections) included on the outer portion of the releaser member 52 engage cooperating abutment structures (e.g., inwardly extending projections) included on the inner portion of the guard extension 37. If the releaser member 52 is unable rotate, an outwardly extending projection of the plunger 26 received in a recess formed in the inner surface of the releaser member 52 is also unable to rotate. If this projection on the plunger 26 cannot rotate, then it cannot slide into a longitudinal opening in the plunger guide 60. If the projection cannot move in this manner, then plunger 26 also cannot move. If the plunger 26 cannot move, the plunger biasing member 50 cannot expand and de-energize. Thus, the releaser member 52 retains the plunger biasing member 50 in the energized state until the guard extension 37 moves to an axial position where the cooperating abutment structures on the outer portion of the releaser member 52 and the inner portion of the guard extension 37 disengage from each and thereby permit the releaser member 52 to rotate relative to the guard extension 37.

Having described the general configuration of the drug delivery device 10, a general method of using the drug delivery device 10 to perform an injection will now be described. As a preliminary step, the user may remove the drug delivery device 10 from any secondary packaging, such as a plastic bag and/or cardboard box. Also, as a preliminary step, the user may prepare the injection site, e.g., by rubbing the patient's skin with an alcohol wipe. Next, the user may pull and detach the removable cap 19 from the housing 12, as described below in more detail. As a result of this motion, the gripper 13 may pull and detach the removable sterile barrier 21 from the drug storage container 20. This may uncover the insertion end 28 of the delivery member 16. Nevertheless, the insertion end 28 of the delivery member 16 will remain surrounded by the guard member 32 at this stage because the guard member 32 is arranged in the extended position. Next, the user may position the drug delivery device 10 over the injection site and then push the distal end of the guard member 32 against the injection site. The force applied by the user will overcome the biasing force of the guard biasing member 35 and the biasing force of the lock ring biasing member 51, thereby causing the guard member 32 to retract into the opening 14 moving from the extended position to the retracted position in the proximal direction. The delivery member 16 remains stationary relative to the housing 12 during the retracting movement of the guard member 32.

Movement of the guard member 32 from the extended position to the retracted position may cause several actions to occur. Because the delivery member 16 remains stationary relative to the housing 12 during retraction of the guard member 32, the insertion end 28 of the delivery member 16 is caused to extend through an opening in the distal end of the guard member 32, thereby piercing the patient's skin at the injection site and penetrating into the patient's subcutaneous tissue. In addition, retraction of the guard member 32 may also activate the drive mechanism 30 to expel the drug 22 from the drug storage container 20.

When the guard member 32 moves from the extended position to the retracted position, the guard member 32 may push the guard extension 37 in the proximal direction. During proximal movement of the guard extension 37, the above-mentioned cooperating abutment structures on the outer portion of the releaser member 52 and the inner portion of the guard extension 37 may slide past one another until they are no longer in contact with one another. When that occurs, the releaser member 52 may be free to rotate about the longitudinal axis A. Rotation of the releaser member 52 at the present stage is caused by the plunger biasing member 50 expanding and pushing a distally facing camming surface included in on the plunger 26 to slide along a proximally facing camming surface on the plunger guide 60. The resulting camming action causes the plunger 26 to rotate, which, in turn, may cause the releaser member 52 to jointly rotate.

Joint rotation of the releaser member 52 and the plunger 26 may continue until the distally facing camming surface included in on the plunger 26 reaches the end of the proximally facing camming surface on the plunger guide 60 and moves into a longitudinal slot formed in the plunger guide 60. The longitudinal slot does not inhibit linear movement of the plunger 26. As consequence, the plunger 26 is driven by the expanding plunger biasing member 50 to translate linearly in the distal direction. As a consequence, the plunger 26 comes into contact with the stopper 24 (if it is not already in contact with the stopper 24) and thereafter pushes the stopper 24 in the distal direction to expel the drug 22 from the drug storage container 20 through the delivery member 16 and out of the insertion end 28 into the patient's tissue. Drug delivery may carry on until the stopper 24 reaches the end-of-dose position. Here, the stopper 24 may abut against a proximally facing portion of the interior surface 15 of the wall of the drug storage container 20. As a result, the plunger 26 ceases moving in the distal direction.

After delivery is complete, the user may then lift the drug delivery deice 10 off of the injection site. With nothing to resist it, the guard biasing member 35 may push the guard member 32 from the retracted position to the extended position to cover the insertion end 28 of the delivery member 16. In some embodiments, this movement of the guard member 32 may cause the lock ring 40 to rotate to a position where it prevents subsequent retraction of the guard member 32.

These and other aspects of an exemplary drug delivery device are discussed in more detail in U.S. patent application Ser. No. 17/036,690, filed Sep. 29, 2020, U.S. patent application Ser. No. 17/035,851, filed Sep. 29, 2020, U.S. patent application Ser. No. 17/035,927, filed Sep. 29, 2020, U.S. patent application Ser. No. 17/036,129, filed Sep. 29, 2020, and U.S. patent application Ser. No. 17/036,217, filed Sep. 29, 2020, the entire contents of each of which are incorporated by reference.

Turning to FIGS. 3-19, additional embodiments of components of the above-described drug delivery device will now be described. Components illustrated in FIGS. 3-19 may be similar or identical in structure, configuration, and/or function to components described above in conjunction with FIGS. 1 and 2. Such components are assigned with the same reference numeral as used in FIGS. 1 and 2, except incremented by 100 or a multiple thereof. A description of certain of these components is abbreviated or eliminated in the interest of conciseness. Details of the structure, configuration, and/or function that differentiate the components illustrated in FIGS. 3-19 from the components in FIGS. 1 and 2 are the focus of the discussion below.

Figures 3, 4:
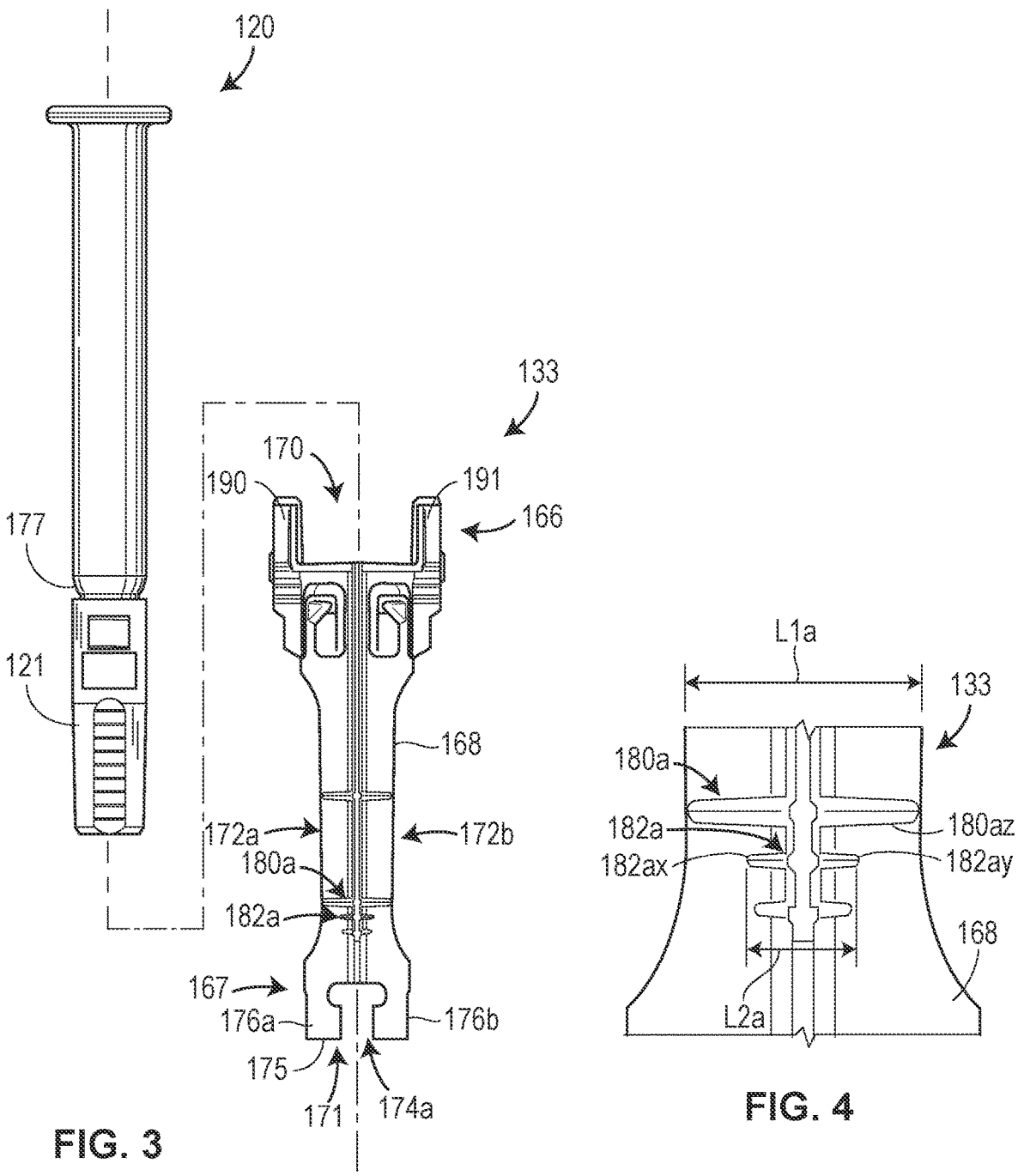
FIG. 3 is a perspective view of an exemplary syringe holder and an exemplary syringe prior to their assembly in a drug delivery device in accordance with various embodiments.
FIG. 4 is an enlarged view of a portion of the syringe holder of FIG. 3.
Figure 5:
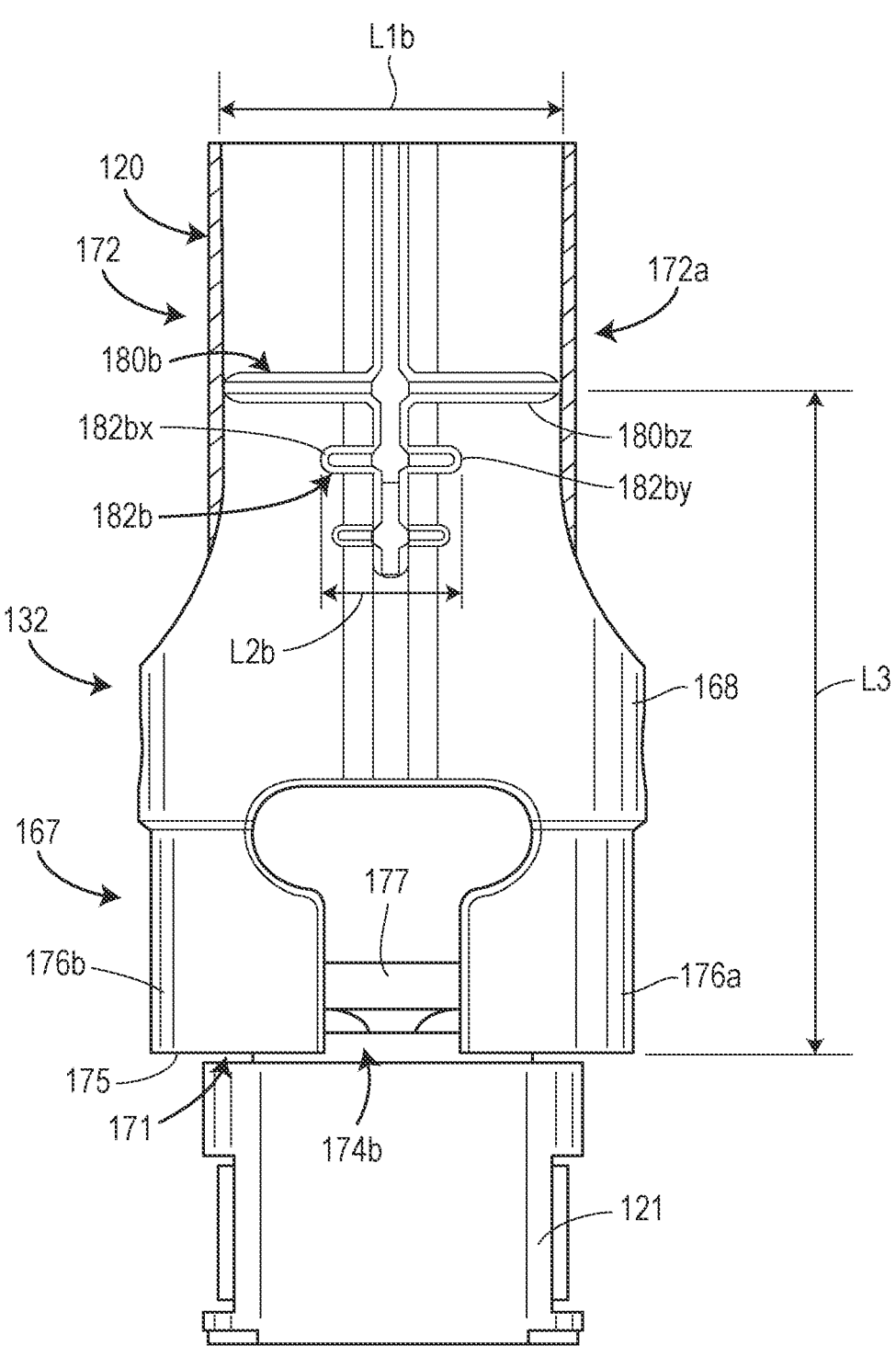
FIG. 5 is a perspective view of a portion of the syringe holder of FIG. 3 and a portion of the syringe of FIG. 3 during and/or after their assembly.

As described above, it may be useful during the assembly of a drug delivery device to arrange a syringe holder at different axial positions with respect to a longitudinal axis of a housing. FIGS. 3-5 illustrate a syringe holder 133 having features to facilitate this objective and other advantageous features.

The syringe holder 133 may have a hollow, generally elongate shape extending along a longitudinal axis between a proximal end 166 and a distal end 167. As an example, the syringe holder 133 may include a wall 168 having a generally annular shape (e.g., a tubular shape) and defining a hollow interior (e.g., an interior space or cavity) of the syringe holder 133. As a more specific example, the wall 168 may surround and/or be centered about the longitudinal axis of the syringe holder 133. The longitudinal axis of the syringe holder 133 may be parallel to, parallel to but offset from, and/or coaxial with the longitudinal axis A of a housing of the drug delivery device (e.g., the housing 12 described above or the housing 112 described below) when the syringe holder 133 is assembled into the housing of the drug delivery device.

An axial opening 170 may be formed in the proximal end 166 of the syringe holder 133 to permit insertion of a syringe 120 into the hollow interior of the syringe holder 133. An axial opening 171 may be formed in the distal end 167 of the syringe holder 133 to permit a removable sterile barrier 121 (e.g., a rigid needle shield (RNS), a non-rigid needle shield (nRNS), etc.) to extend partially or entirely outside of the syringe holder 133 when the syringe is fully inserted into the syringe holder 133, as seen in FIG. 5.

Referring to FIGS. 3-5, one or more side openings may be formed in the wall 168 of the syringe holder 133 and may communicate with the hollow interior of the syringe holder 133. One of more of these side openings may be located in the axial direction at least partially between the axial opening 170 and the axial opening 171. For example, the syringe holder 133 may include a side opening 172a and/or a side opening 172b formed in the wall 168 approximately midway long the longitudinal axis of the syringe holder 133. The side openings 172a and 172b may be located on opposite sides of the longitudinal axis of the syringe holder 133 and each may have a generally oval shape or a generally rectangular shape when viewed from the side. At least one of the side openings 172a and 172b may align with a side opening 165 formed in a housing 112 of a drug delivery device when the syringe holder 133 is arranged in second axial position or a final assembled position, as described in more detail below with reference to FIGS. 9-14. In addition or as an alternative, the syringe holder 133 may include a side opening 174a and/or a side opening 174b, one or both of which may be partially or entirely distal to the side opening 172a and/or the side opening 172b. The side openings 174a and 174b may be located on opposite sides of the longitudinal axis of the syringe holder 133 and each may have a generally C-shape or U-shape when viewed from the side, as seen in FIGS. 3 and 5. Furthermore, as illustrated in FIGS. 3 and 5, the side openings 172a, 172b, 174a, and 174b may be arranged at respective circumferential positions around the longitudinal axis of the syringe holder 133 such that, for example, treating a center of the side opening 172a as corresponding to zero degrees and moving in the circumferential direction, a center of the side opening 174a may be located at approximately 90 degrees, a center of the side opening 172b may be located at approximately 180 degrees, and a center of the side opening 174b may be located at approximately 270 degrees. Each of the side openings 174a and 174b may be formed at least partially in a distally directed end surface 175 of the syringe holder 133, and, as a consequence, may divide at least a portion of the wall 168 at the distal end 167 of the syringe holder 133 into a pair of axially extending arms 176a and 176b.

One or both of the axially extending arms 176a and 176b may be configured to flex (e.g., elastically deform) in at least a radial direction with respect to the longitudinal axis of the syringe holder 133 during the insertion of the syringe 120 into the syringe holder 133. For example, when the removable sterile barrier 120 of the syringe 120 is pushed in the axial direction through the space between the axially extending arms 176a and 176b, the axially extending arms 176a and 176b may flex radially outwardly. Once the removable sterile barrier 120 has cleared the axially extending arms 176a and 176b and is entirely distal to the axially extending arms 176a and 176b (as seen in FIG. 5), the axially extending arms 176a and 176b may flex radially inwardly back to their original shape, including, for example, snapping back to their original shape. The axially extending arms 176a and 176b and/or other portions or an entirety of the syringe holder 133 may be made of a resilient material to facilitate said flexing during the insertion of the syringe 120.

Inner portion(s) of the axially extending arms 176a and/or 176b may be configured to cooperate with (e.g., contact, abut against, secure, couple with, and/or grip) an outer portion of the syringe 120 to support the syringe 120 within the syringe holder 133. As an example, the inner portion of the axially extending arms 176a and/or 176b may be configured to contact a generally distally directed surface 177 of the syringe 120 to prevent movement of the syringe 120 in the distal direction with respect to the syringe holder 133. As a more specific example, one or both of the axially extending arms 176a and/or 176b may include an inwardly extending protrusion (e.g., a rib, tab, finger, flange, collar, lip, and/or any other suitable structure) having a proximally directed surface configured to contact the distally directed surface 177 of the syringe 120. This inwardly extending protrusion may extend generally radially inwardly with respect to the longitudinal axis of the syringe holder 133 and/or extend inwardly in any direction that is non-parallel to the longitudinal axis of the syringe holder 133. As an even more specific example, the distally directed surface 177 of the syringe 120 may be part of the neck of the syringe 120, as shown in FIGS. 3 and 5. As a further example, an inner diameter or other inner dimension defined between an inwardly extending protrusion of the axially extending arm 176a and an inwardly extending protrusion of the axially extending arm 176b may be less than: (a) an outer diameter or other outer dimension of a portion of a barrel of the syringe 120 that is proximal to the neck of the syringe 120, and/or (b) an outer diameter or other outer dimension of the removable sterile barrier 121.

Outer portion(s) of the wall 168 of the syringe holder 133 may be configured to cooperate with (e.g., contact, abut against, secure, couple with, and/or grip) a first inner portion of the housing 112 to support the syringe holder 133 at a first axial position (e.g., a proximal position or an intermediate position) and/or a first rotational position with respect to the housing 112 and/or cooperate with (e.g., contact, abut against, secure, couple with, and/or grip) a second inner portion of the housing 112 to support the syringe holder 133 at a second axial position (e.g., a distal position or a final assembled position) and/or a second rotational position with respect to the housing 112. As an example, the syringe holder 133 may include an outwardly extending protrusion 180a and/or an outwardly extending protrusion 180b, as seen in FIGS. 3-5. The outwardly extending protrusions 180a and 180b may be disposed on opposite sides of the longitudinal axis of the syringe holder 133. The outwardly extending protrusions 180a and 180b each may extend generally radially outwardly with respect to the longitudinal axis of the syringe holder 133 and/or extend outwardly in any direction that is non-parallel to the longitudinal axis of the syringe holder 133. The outwardly extending protrusions 180a and/or 180b each may be configured as a rib, tab, finger, flange, lip, collar, and/or any other suitable structure. The outwardly extending protrusions 180a and 180b may have, respectively, a distally directed surface 180az and a distally directed surface 180bz. As described below in more detail, the distally directed surface 180$az$ and the distally directed surface 180$bz$ may contact respective proximally directed surfaces of the housing 112 to prevent movement of the syringe holder 133 in at least the distal direction when the syringe holder 133 is arranged in the first axial position within the housing 112. As an example, the distally directed surfaces 180$az$ and 180$bz$ may abut against the respective proximally directed surfaces of the housing 112 to prevent distal movement of the syringe holder 133 with respect to the housing 112.

The outwardly extending protrusions 180$a$ and 180$b$ may have, respectively, a length L1$a$ and a length L1$b$ measured generally in a circumferential direction of the syringe holder 133, as seen in FIGS. 4 and 5. As an example, the length L1$a$ and/or the length L1$b$ may correspond to an arc length measured with respect to the longitudinal axis of the syringe holder 133. Alternatively, the length L1$a$ and/or the length L1$b$ may correspond to a linear distance.

In addition to or as an alternative to the outwardly extending protrusions 180$a$ and 180$b$, the syringe holder 133 may include outwardly extending protrusions 182$a$ and 182$b$. The outwardly extending protrusions 182$a$ and 182$b$ may be disposed on opposite sides of the longitudinal axis of the syringe holder 133. The outwardly extending protrusions 182$a$ and 182$b$ each may extend generally radially outwardly with respect to the longitudinal axis of the syringe holder 133 and/or extend outwardly in any direction that is non-parallel to the longitudinal axis of the syringe holder 133. The outwardly extending protrusions 182$a$ and/or 182$b$ each may be configured as a rib, tab, finger, flange, lip, collar, and/or any other suitable structure. As seen in FIGS. 3-5, the outwardly extending protrusion 182$a$ may be adjacent and distal to the outwardly extending protrusion 180$a$, and the outwardly extending protrusion 182$b$ may be adjacent and distal to the outwardly extending protrusion 180$b$.

The outwardly extending protrusion 182$a$ may have side surfaces 182$ax$ and 182$ay$, each of which may face generally in the circumferential direction. Similarly, the outwardly protrusion 182$b$ may have side surfaces 182$bx$ and 182$by$, each of which may face generally in the circumferential direction. As described below in more detail, one or more of the side surfaces 182$ax$, 182$ay$, 182$bx$, and 182$by$ may contact respective circumferentially facing surfaces of an inner portion of the housing 112 to prevent rotation of the syringe holder 133 in one or more rotational directions when the syringe holder 133 is arranged in the first axial position within the housing 112.

The outwardly extending protrusions 182$a$ and 182$b$ may have, respectively, a length L2$a$ and a length L2$b$ measured generally in a circumferential direction of the syringe holder 133, as seen in FIGS. 4 and 5. As an example, the length L2$a$ and/or the length L2$b$ may correspond to an arc length measured with respect to the longitudinal axis of the syringe holder 133. Alternatively, the length L2$a$ and/or the length L2$b$ may correspond to a linear distance. In some embodiments, the length L1$a$ of the outwardly extending protrusion 180$a$ may be larger than the length L2$a$ of the outwardly extending protrusion 182$a$, and/or the length L1$b$ of the outwardly extending protrusion 180$b$ may be larger than the length L2$b$ of the outwardly extending protrusion 182$b$. These relative lengths of the outwardly extending protrusions may facilitate, when the syringe holder 133 is in the first axial position, an ability of the outwardly extending protrusions 180$a$ and/or 180$b$ to prevent distal movement of the syringe holder 133 with respect to the housing 112 and/or an ability of the outwardly extending protrusions 182$a$ and/or 182$b$ to prevent rotational movement of the syringe holder 133 with respect to the housing 112, as described in more detail below.

Figure 6:
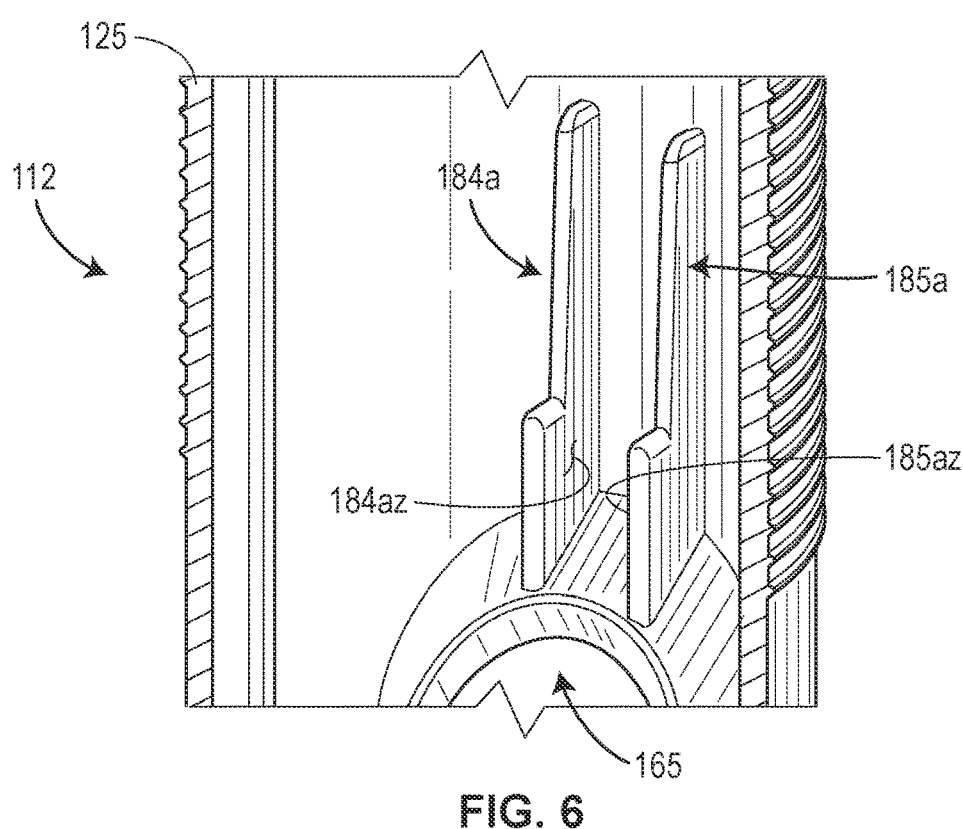
FIG. 6 is a cutaway perspective view of a proximal portion of a housing of a drug delivery device in accordance with various embodiments.
Figure 7:
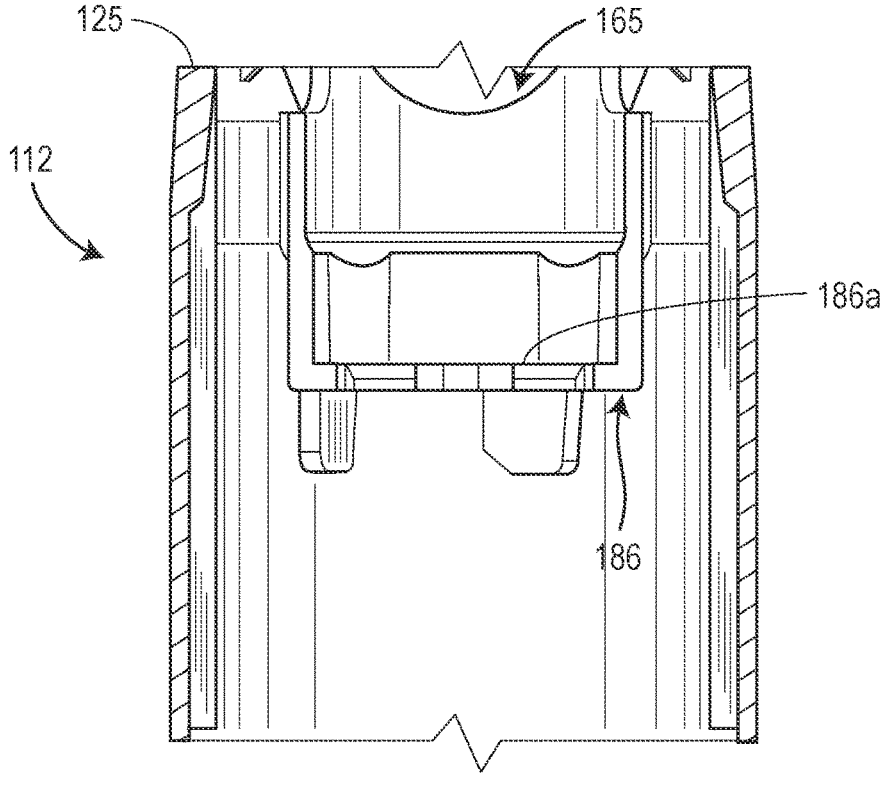
FIG. 7 is a cutaway perspective view of a distal portion of the housing of FIG. 6.
Figure 8:
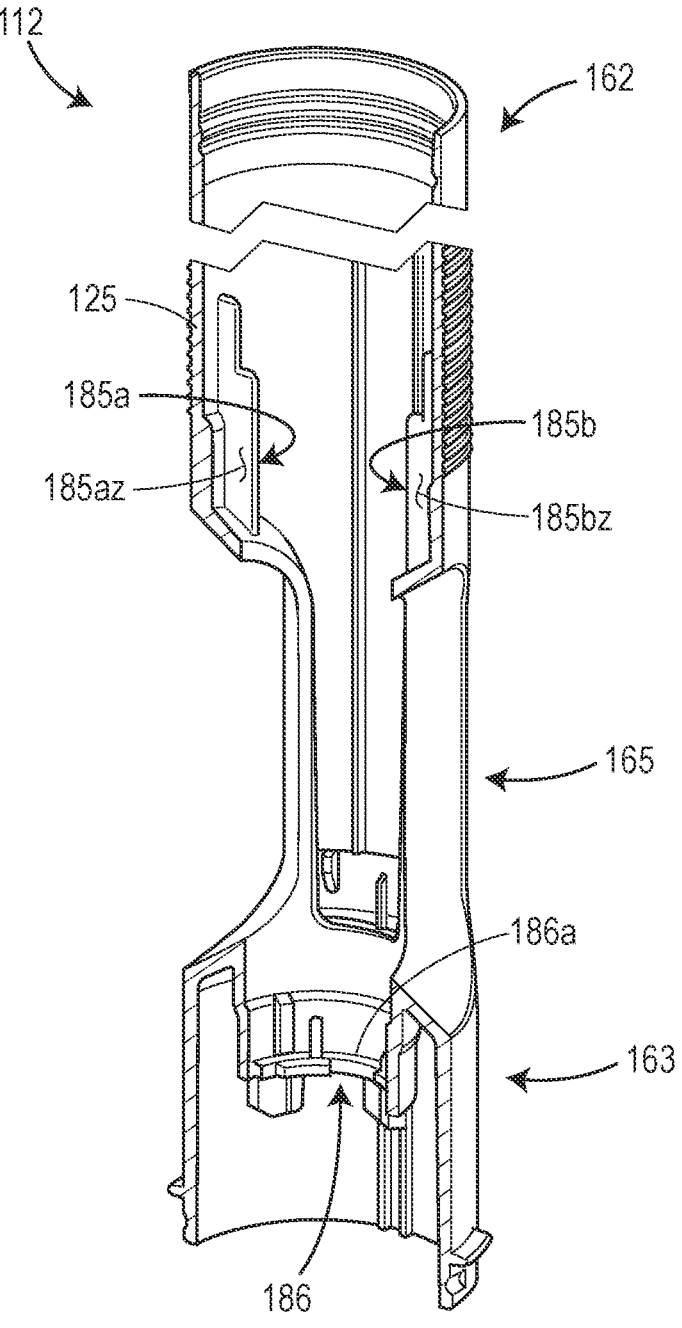
FIG. 8 is a cutaway perspective view of the housing shown partially in FIGS. 6 and 7.

Referring to FIGS. 6-9, an embodiment of the housing 112 configured to cooperate in various ways with the syringe holder 133 will now be described. FIG. 6 illustrates a cutaway view of a proximal portion of the housing 112 prior to insertion of the syringe holder 133, and FIG. 7 illustrates a cutaway view of a distal portion of the housing 112 prior to insertion of the syringe holder 133. FIG. 8 illustrates another cutaway view of the housing 112 prior to insertion of the syringe holder 133. The syringe holder 133, the housing 112, the syringe 120 and/or other related components may correspond to a subassembly of the drug delivery device.

Figure 9:
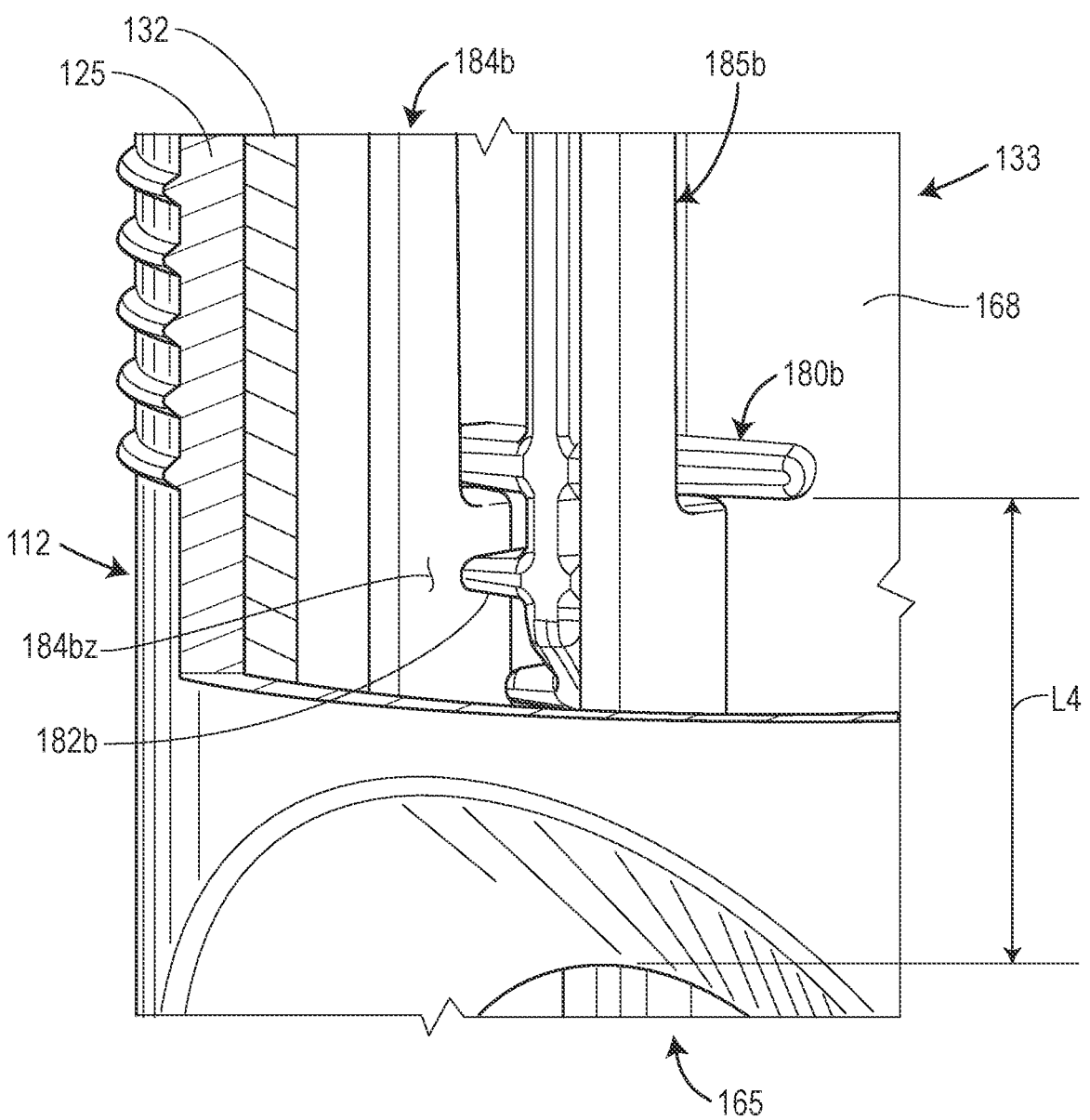
FIG. 9 is a cutaway perspective view of the syringe holder of FIGS. 3-5 arranged in a first axial position within the housing of FIGS. 6-8.

As mentioned above, inner portion(s) of the wall 125 of the housing 112 may be configured to cooperate with (e.g., contact, abut against, secure, couple with, and/or grip) one or more of the outwardly extending protrusions 180$a$ and 180$b$ of the syringe holder 133 in order to support the syringe holder 133 at a first axial position with respect to the housing 112 and/or a first rotational position with respect to the housing 112. As an example, the housing 112 may include an inwardly extending protrusion 184$a$, an inwardly extending protrusion 185$a$, an inwardly extending protrusion 184$b$, and an inwardly extending protrusion 185$b$, as seen in FIGS. 6, 8, and 9. The inwardly extending protrusions 184$a$ and 185$a$ may be located on one side of the longitudinal axis of the housing 112, and the inwardly extending protrusions 184$b$ and 185$b$ may be located on an opposite side of the longitudinal axis of the housing 112. The inwardly extending protrusions 184$a$, 185$a$, 184$b$, and/or 185$b$ may be proximal to the side opening 165, as illustrated in FIGS. 6, 8, and 9. The inwardly extending protrusions 184$a$, 185$a$, 184$b$, and/or 185$b$ may extend generally radially inwardly with respect to the longitudinal axis of the housing 112 and/or extend inwardly in any direction that is non-parallel to the longitudinal axis of the housing 112. The inwardly extending protrusions 184$a$, 185$a$, 184$b$, and/or 185$b$ each may be configured as a rib, tab, finger, flange, lip, collar, and/or any other suitable structure. The inwardly extending protrusions 184$a$, 185$a$, 184$b$, and 185$b$ may possess, respectively, proximally directed surfaces 184$az$, 185$az$, 184$bz$, and 185$bz$.

When the syringe holder 133 has a first rotational position with respect to the housing 112 and is inserted in the distal direction into the housing 112 through the axial opening 164 in the proximal end 162 of the housing 112, the distally directed surface 180$az$ of the outwardly extending protrusion 180$a$ of the syringe holder 133 may come into contact with and/or abut against one or more of the proximally directed surfaces 184$az$ and 185$az$ of the inwardly extending protrusions 184$a$ and 185$a$ and/or the distally directed surface 180$bz$ of the outwardly extending protrusion 180$b$ of the syringe holder 133 may come into contact with and/or abut against one or more of the proximally directed surfaces 184$bz$ and 185$bz$ of the inwardly extending protrusions 184$b$ and 185$b$ as seen in FIG. 9. These point(s) of contact may prevent further distal movement of the syringe holder 133 with respect to the housing 112. This axial position of the syringe holder 133 (shown in FIG. 9) may correspond to the first axial position of the syringe holder 133. When the syringe holder 133 is in the first axial position and the first rotational position, the outwardly extending protrusion 182$b$ of the syringe holder 133 may be disposed in the circumferential direction between the inwardly extending protrusions 184$b$ and 185$b$, as seen in FIG. 9. As an example, the side surfaces 182*bx* and 182*by* of the outwardly extending protrusion 182*b* may face, contact, and/or abut against, respectively, a side surface of the inwardly extending protrusion 184*b* and a side surface of the inwardly extending protrusion 185*b*. As an example, the outwardly extending protrusion 182*b* when positioned between the inwardly extending protrusions 184*b* and 185*b* may form an interference-fit (e.g., a press-fit, friction-fit, and/or snap-fit) with the inwardly extending protrusions 184*b* and 185*b*. A similar arrangement may, but is not required to, exist for the outwardly extending protrusion 182*a* and the inwardly extending protrusions 184*a* and 185*a*. This configuration of the outwardly extending protrusions 182*a* and/or 184*b* with respect to the inwardly extending protrusions 184*a*, 185*b*, 184*b*, and/or 185*b* when the syringe holder 133 is in the first axial position may prevent the syringe holder 133 from rotating with respect to the housing 112. This, in turn, may reduce the likelihood of the syringe holder 133 becoming inadvertently moved out of the first axial position and/or the first rotational position due to, for example, jostling, vibrations, and/or sudden movements during the manufacturing process, while nevertheless permitting the syringe holder 133 to be intentionally moved in the proximal direction when desired. As described in more detail below, one may move the syringe holder 133 in the proximal direction and then rotate the syringe holder 133 from the first rotational position to a second rotational position where no portion of the outwardly extending protrusion 180*a* aligns in the circumferential direction with the inwardly extending protrusions 184*a* and 185*a* and no portion of the outwardly extending protrusion 180*b* aligns in the circumferential direction with the inwardly extending protrusions 184*b* and 185*b*. As a result, it may be possible when the syringe holder 133 is in the second rotational position to move the syringe holder 133 in the distal direction without such distal movement being prevented by contact between the outwardly extending protrusion 180*a* and the inwardly extending protrusions 184*a* and 185*a* and/or contact between the outwardly extending protrusion 180*b* and the inwardly extending protrusions 184*b* and 185*b*.

When the syringe holder 133 is in the first axial position, at least a portion of the distal end 167 of the syringe holder 133 may be aligned with the side opening 165 of the housing 112. As an example, a portion or the entirety of the side opening 172*b* may be aligned with the side opening 165 of the housing 112 when the syringe holder 133 is in the first axial position. In order to achieve this configuration, some embodiments of the syringe holder 133 and the housing 112 may be dimensioned as follows. The syringe holder 133 may have a length L3 defined in the axial direction between the distally directed surface 180*bz* of the outwardly extending protrusion 180*b* and the distally directed end surface 175 of the syringe holder 133, as seen in FIG. 5. The housing 112 may have a have a length L4 defined in the axial direction between the proximally directed surfaces 184*bz*, 185*bz* and the proximal-most end of the side opening 165, as seen in FIG. 9. L3 may be larger than L4 such that a portion of or the entirety of the distal end 167 of the syringe holder 133, including, for example, a portion of or the entirety of the side opening 172*b* of the syringe holder 133, is aligned with the side opening 165 of the housing 112 when the syringe holder 133 is in the first axial position. Similar dimensioning may, but is not required to, be used for the distally directed surface 180*az* of the outwardly extending protrusion 180*a* and the distally directed end surface 175 of the syringe holder 133.

Inner portion(s) of the wall 125 of the housing 112 may be configured to cooperate with (e.g., contact, abut against, secure, couple with, and/or grip) the distally directed end surface 175 of the syringe holder 133 in order to support the syringe holder 133 at a second axial position (e.g., a distal position or a final assembled position) with respect to the housing 112 and/or a second rotational position with respect to the housing 112. As an example, the housing 112 may include an inwardly extending protrusion 186, as seen in FIG. 7. The inwardly extending protrusions 186 may be distal to the side opening 165 and/or distal to the inwardly extending protrusions 184*a,b* and 185*a,b*. The inwardly extending protrusion 186 may extend generally radially inwardly with respect to the longitudinal axis of the housing 112 and/or extend inwardly in any direction that is non-parallel to the longitudinal axis of the housing 112. The inwardly extending protrusion 186 may be configured as a rib, tab, finger, flange, lip, collar, and/or any other suitable structure. The inwardly extending protrusion 186 may possess proximally directed surface 186*a*.

During an assembly process, as described in more detail below, the syringe holder 133 may be moved in the distal direction until the distally directed end surface 175 of the syringe holder 133 comes into contact with and/or abuts against the proximally directed surface 186*a* of the inwardly extending protrusion 186 of the housing 112. This contact may prevent further distal movement of the syringe holder 133 with respect to the housing 112. This axial position of the syringe holder 133 may correspond to the second axial position of the syringe holder 133. In some embodiments, the second axial position may correspond to the final assembled position of the syringe holder 133. In embodiments where the syringe holder 133 does not move with respect to the housing 112 during operation of the drug delivery device, the syringe holder 133 may remain in the second axial position throughout the life of the drug delivery device. In embodiments where the syringe holder 133 does move with respect to the housing 112 during operation of the drug delivery device (e.g., distal movement to achieve needle insertion), the syringe holder 133 may not remain in the second axial position throughout the life of the drug delivery device. In some embodiments, the proximally directed surface 186*a* of the inwardly extending protrusion 186 of the housing 112 may be configured to contact the distally directed end surface 175 of the syringe holder 133 regardless of whether or not the syringe holder 133 is in a first rotational position or the second rotational position; whereas, in other embodiments, the proximally directed surface 186*a* of the inwardly extending protrusion 186 of the housing 112 may be configured to contact the distally directed end surface 175 of the syringe holder 133 only if the syringe holder 133 is in the second rotational position.

Figure 15:
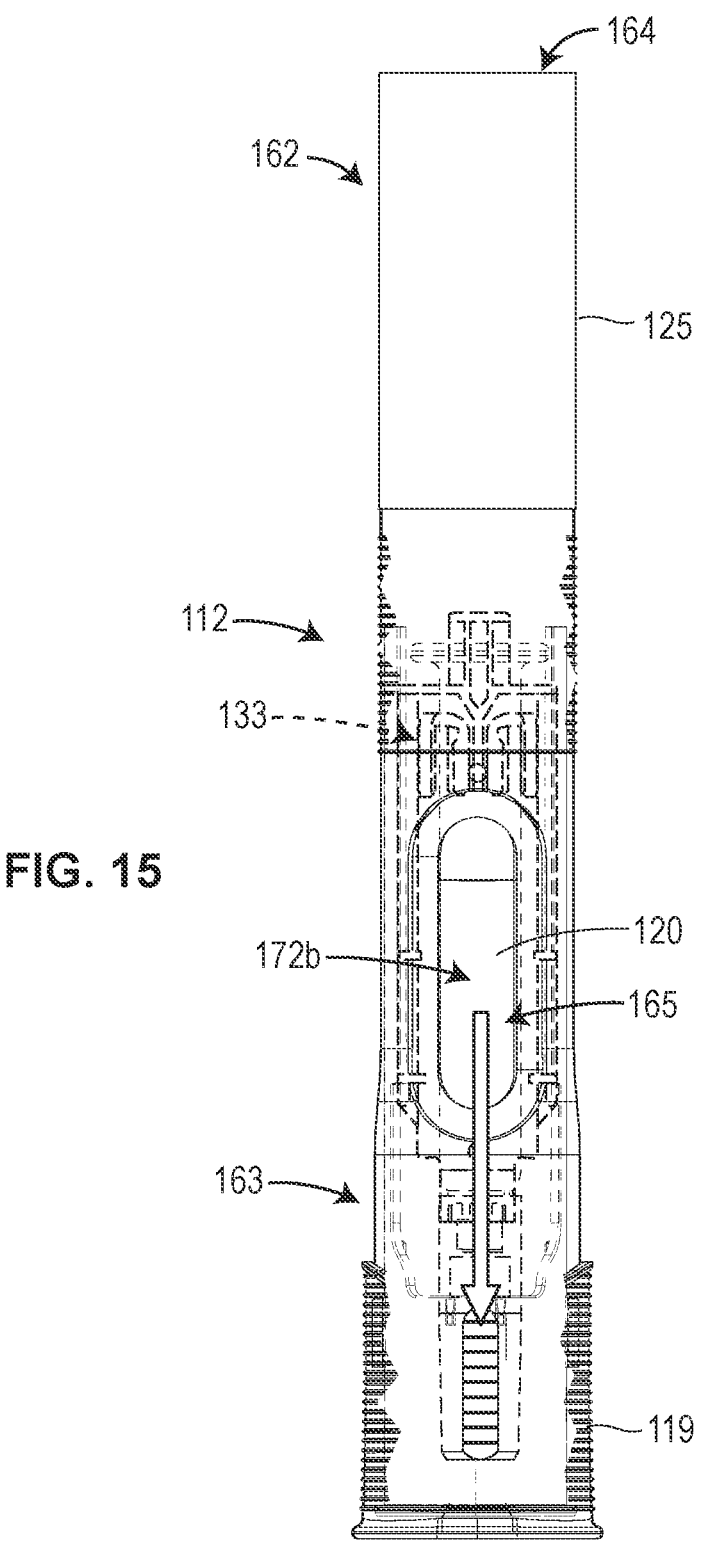

When the syringe holder 133 is in the second axial position, at least a portion of the distal end 167 of the syringe holder 133 may be distal to the side opening 165 of the housing 112. As an example, a portion or the entirety of the side opening 172*b* may be distal to the side opening 165 of the housing 112 when the syringe holder 133 is in the second axial position, as seen in FIG. 15.

Methods of assembling the syringe holder 133 into the housing 112 will now be described with reference to FIGS. 10-15. The process of assembling the syringe holder 133 into the housing 112 may be a part or aspect of an overall process of assembling a drug delivery device such as the drug delivery device 10 described above. FIGS. 10-15 illustrate respective steps or stages of the method of assembly and are arranged in chronological order. Some or all of the steps described below may be performed manually by a person and/or automatically by a machine.

Figure 10:
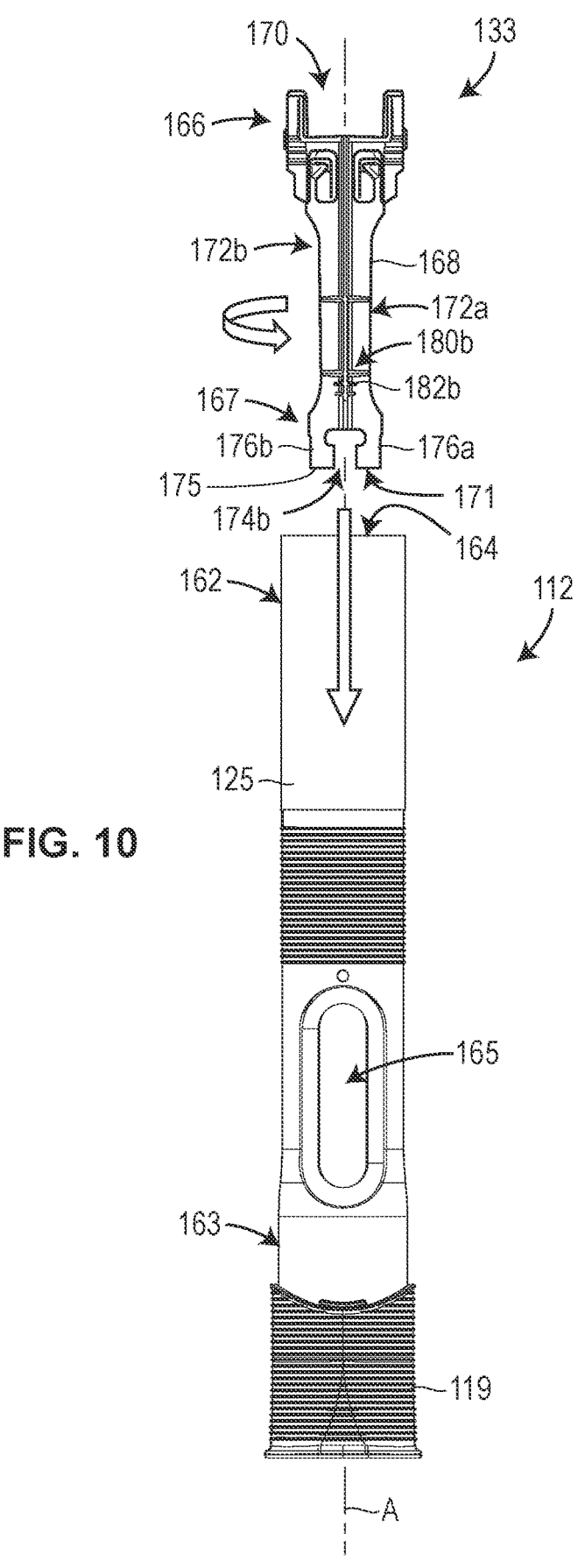
FIG. 10-15 illustrate steps of an exemplary method of assembling a syringe holder into a housing of a drug delivery device in accordance with various embodiments.

Referring to FIG. 10, an initial step may involve arranging the syringe holder 133 in the first rotational position (e.g., an intermediate rotational position) with respect to the housing 112. As an example, this step may involve rotating the syringe holder 133 with respect to the housing 112 prior to and/or substantially simultaneously with inserting the syringe holder 133 into the housing 112. The removable cap 119 may be coupled to the distal end 163 of the housing 112 to cover an axial opening (e.g., the axial opening 14 described above) in the distal end 163 of the housing 112 prior to this step.

Figure 11:
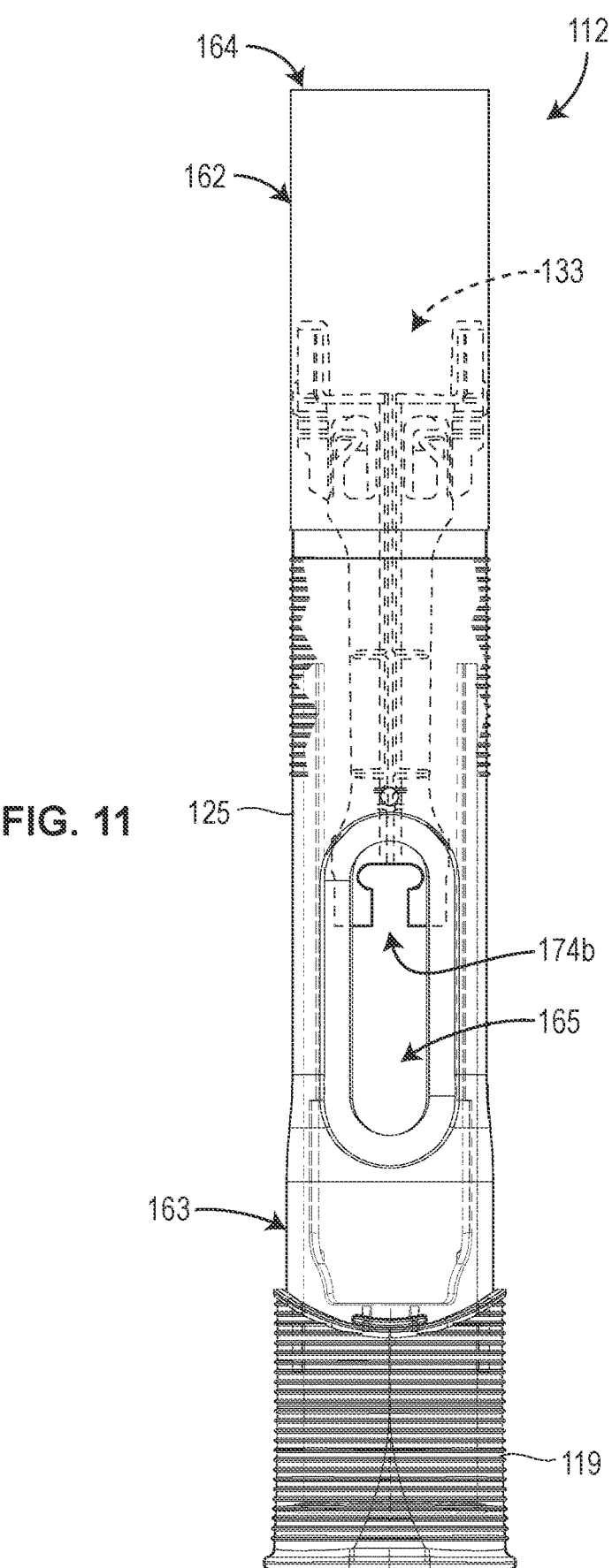

After and/or substantially simultaneously with arranging the syringe holder 133 in the first rotational position, the syringe holder 133 may be inserted into the hollow interior of the housing 112 and secured in a first axial position, as depicted in FIG. 11. As an example, the syringe holder 133 may be moved in the distal direction along the longitudinal axis A of the housing 112 through the axial opening 164 in the proximal end 162 of the housing 112. As a more specific example, the distal end 167 of the syringe holder 133 may be the leading end of the syringe holder 133 to enter the interior of the housing 112 through the axial opening 164. As an even more specific example, the syringe holder 133 may be moved in the distal direction until the distally directed surface 180az of the outwardly extending protrusion 180a of the syringe holder 133 comes into contact with and/or abuts against one or more of the proximally directed surfaces 184az and 185az of the inwardly extending protrusions 184a and 185a of the housing 112 and/or the distally directed surface 180bz of the outwardly extending protrusion 180b of the syringe holder 133 comes into contact with and/or abuts against one or more of the proximally directed surfaces 184bz and 185bz of the inwardly extending protrusions 184b and 185b. Further distal movement of the syringe holder 133 with respect to the housing 112 may be at least temporarily prevented as a result of this contact.

Securing the syringe holder 133 in the first axial position may optionally involve arranging the outwardly extending protrusion 182a of the syringe holder 133 between the inwardly extending protrusions 184a and 185a of the housing 112 and/or arranging the outwardly extending protrusion 182b of the syringe holder 133 between the inwardly extending protrusions 184b and 185b of the housing 112. The outwardly extending protrusion 182a may naturally come to be positioned between the inwardly extending protrusions 184a and 185a if the syringe holder 133 is arranged in the first rotational position when it is inserted in the distal direction into the housing 112. The same applies to the outwardly extending protrusion 182a and the inwardly extending protrusions 184b and 185b. As an example, the outwardly extending protrusion 182a may be inserted between the inwardly extending protrusions 184a and 185a to form an interference-fit (e.g., a press-fit, friction-fit, and/or snap-fit) with the inwardly extending protrusions 184a and 185a and/or the outwardly extending protrusion 182b may be inserted to between the inwardly extending protrusions 184b and 185b to form an interference-fit (e.g., a press-fit, friction-fit, and/or snap-fit) with the inwardly extending protrusions 184b and 185b. As a result of these interference-fit(s), the syringe holder 133 may be held relatively securely (but not necessarily permanently) in the first axial position and/or the first rotational position.

By arranging the syringe holder 133 in the first axial position and the first rotational position, the side opening 172b of the syringe holder 133 may come to be aligned with the side opening 165 of the housing 112 when the syringe holder 133, as seen in FIG. 11. Additionally or alternatively, the side opening 172a of the syringe holder 133 may come to be aligned with a side opening (not illustrated) of the housing 112 located across the longitudinal axis A from the side opening 165.

Figure 12:
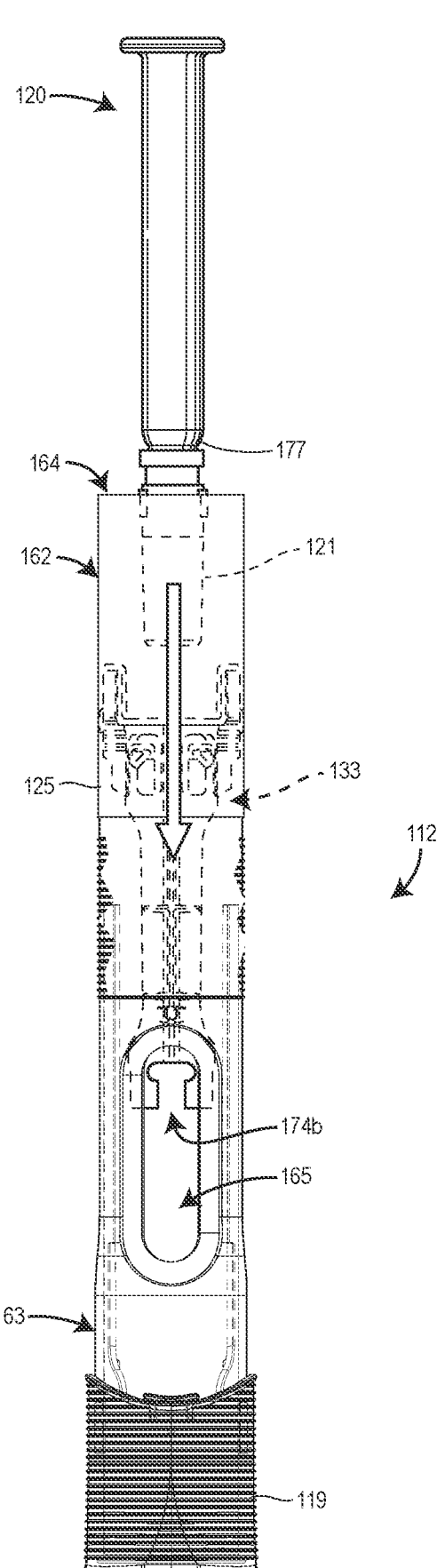

After the syringe holder 133 has been secured in the first axial position and the first rotational position, the syringe 120 may be inserted into the hollow interior of the syringe holder 133 as shown in FIG. 12. As an example, the syringe 120 may be moved in the distal direction along the longitudinal axis A of the housing 112 and/or syringe holder 133 and enter the interior of the syringe holder 133 through the axial opening 170 in the proximal end 166 of the syringe holder 133. As a more specific example, the removable sterile barrier 121 mounted at the distal end of the syringe 120 may be the first portion of the syringe 120 to enter the interior of the syringe holder 133. As an even more specific example, the syringe 120 may be moved in the distal direction until a distally directed surface 177 of the syringe 120 comes into contact with and/or abuts an inwardly extending protrusion disposed at the distal end 167 of the syringe holder 133. Further distal movement of the syringe 120 with respect to the syringe holder 133 may be substantially impeded but not necessarily prevented once this contact occurs. As described above, inserting the removable sterile barrier 121 through the syringe 133 may cause the axially extending arms 176a and 176b to flex outwardly, and, once the removable sterile barrier 121 has moved beyond the axially extending arms 176a and 176b in the distal direction, the axially extending arms 176a and 176b may flex back inwardly due to, for example, their elasticity. During insertion of the syringe 120 into the syringe holder 133, the syringe holder 133 may not move axially and/or rotationally with respect to the housing 112 (and thus remain stationary in the first axial position and/or the first rotational position) due at least in part to the contact between the outwardly extending protrusions 180a,b and 182a,b of the syringe holder 133 and the inwardly extending protrusions 184a,b and 185a,b of the housing 112.

When the syringe holder 133 is arranged in the first axial position, a radially outwardly facing surface of each of the axially extending arms 176a and 176b may be spaced from a radially inwardly facing surface of the housing 112 by a radial distance such that the axially extending arms 176a and 176b can flex radially outwardly to accommodate insertion of the removable sterile barrier 121 through the distal end 167 of the syringe holder 133. When the syringe holder 133 is arranged in the second axial position (described below), the radial distance between radially outwardly facing surface of the axially extending arms 176a and 176b and the radially inwardly facing surface of the housing 112 may be substantially decreased or eliminated such that the radially inwardly facing surface of the housing 112 prevents the axially extending arms 176a and 176b from flexing radially outwardly, thereby preventing further distal movement of the syringe 120 with respect to the syringe holder 133. As an example, when the syringe holder 133 is arranged in the first axial position, the radially outwardly facing surface of one or both of the axially extending arms 176a and 176b may not contact the radially inwardly facing surface of the housing 112, whereas, when the syringe holder 133 is arranged in the second axial position, the radially outwardly facing surface of one or both of the axially extending arms 176b and 176b may contact and/or abut against the radially inwardly facing surface of the housing 112.

Figure 13:
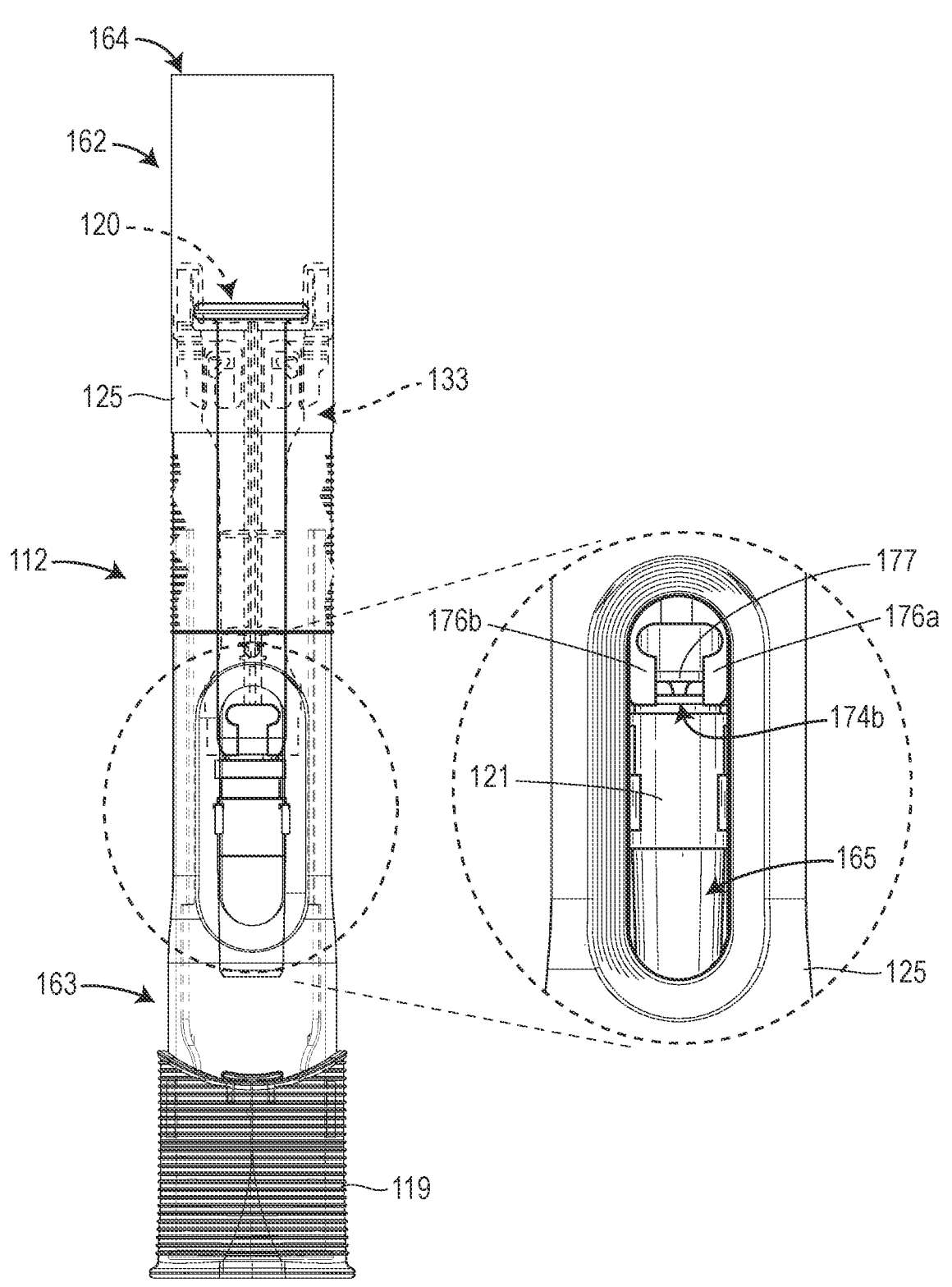

FIG. 13 illustrates the syringe 120 after it has been fully inserted into and is seated within the syringe holder 133. Here, a portion of the syringe 120 may be aligned with the side opening 172*b* of the syringe holder 133. As an example, a portion of a drug inside of the syringe may be aligned with the side opening 172*b*, a portion of the neck of the syringe 120 may be aligned with the side opening 172*b*, and/or a portion of the distally directed surface 177 of the syringe 120 may be aligned with the side opening 172*b*. Additionally or alternatively, a portion of the removable sterile barrier 121 may be aligned with the side opening 172*b* of the syringe holder 133. Because the side opening 172*b* of the syringe holder 133 is aligned with the side opening 165 of the housing 112, the portion of the syringe 120 aligned with the side opening 172*b* and/or the portion of the removable barrier 121 aligned with the side opening 172*b* may be visible to an observer outside of the housing 112 looking through the side opening 165 into the interior of the housing 112.

While the syringe holder 133 is arranged in the first axial position and first rotational position and the syringe 120 is seated within the syringe holder 133 (as depicted in FIG. 13), an inspection of the syringe 120, the syringe holder 133, the removable sterile barrier 121, and/or other components inside of the housing 112 may be performed. As an example, the inspection may involve inspecting at least a portion of the syringe 120 that is aligned with and/or visible through side opening 165 of the housing 112, at least a portion of the syringe holder 133 that is aligned with and/or visible through side opening 165 of the housing 112, and/or at least a portion of the removable sterile barrier 121 that is aligned with and/or visible through side opening 165 of the housing 112. As a more specific example, the inspection may involve inspecting a portion of the syringe 120 and/or removable barrier 21 that is visible through aligned portions of the side opening 172*b* of the syringe holder 133 and the side opening 165 of the housing 112. The inspection may be performed by a person and/or with a machine. The inspection may be performed visually (e.g., optically), audibly, electrically, magnetically, chemically, and/or via any other suitable means of interrogation. The inspection may involve, for example, checking if the syringe 120 and/or removable sterile barrier 121 is properly secured within the syringe holder 133, checking if the syringe holder 133 is properly secured within the housing 112, checking a drug inside of the syringe 120 for particulates, contaminants, and/or other quality and/or safety measures, and/or checking for fractures, cracks, and/or other structural damage in, for example, the syringe 120, the removable sterile barrier 121, and/or the syringe holder 133. As an example, checking if the syringe 120 is properly secured within the syringe holder 133 may involve inspecting an angle, radial position, and/or axial position of the axially extending arms 176*a* and/or 176*b* with respect to, for example, the longitudinal axis of the syringe holder 133. As a more specific example, one may check if the axially extending arms 176*a* and/or 176*b* have flexed (e.g., flexed radially inwardly) back to their original shape. Additionally or alternatively, the inspection may involve checking other components inside of the housing 112 that are aligned with and/or visible through the side opening 165 and/or the side opening 172*b*. To the extent that the housing 112 includes a side opening across the longitudinal axis A from the side opening 165, a similar visual inspection may be performed through that side opening as well.

Figure 14:
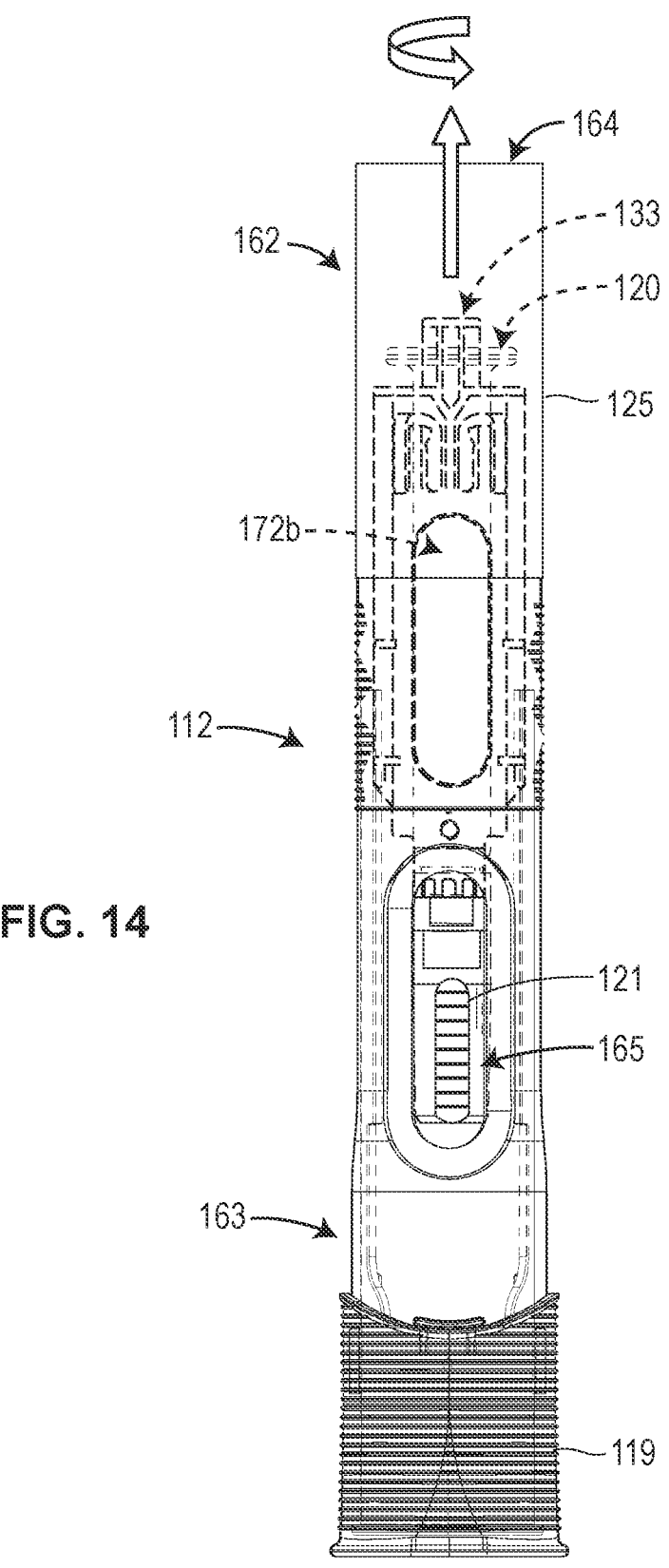

After the inspection is complete, the syringe holder 133 (including the syringe 120) may be moved in the proximal direction away from the first axial position and then rotated from the first rotational position to a second rotational position (e.g., a final rotational position), as seen in FIG. 14.

As an example, the syringe holder 133 may be moved in the proximal direction to an axial position (proximal to the first axial position) where the outwardly extending protrusion 182*a* is no longer between the inwardly extending protrusions 184*a* and 185*a* and the outwardly extending protrusion 182*b* is no longer between the inwardly extending protrusions 184*b* and 185*b*. As a result, the syringe holder 133 may no longer be rotationally restrained by the inwardly extending protrusions 184*a,b* and 185*a,b*. Subsequently, the syringe holder 133 may be rotated into the second rotational position. As an example, in the second rotational position, the outwardly extending protrusion 180*a* may not be aligned in the circumferential direction with the inwardly extending protrusions 184*a* and 185*a* and the outwardly extending protrusion 180*b* may not be aligned in the circumferential direction with the inwardly extending protrusions 184*b* and 185*b*. Stated another way, in the second rotational position, the outwardly extending protrusion 180*a* may be rotationally offset from the inwardly extending protrusions 184*a* and 185*a* and the outwardly extending protrusion 180*b* may be rotationally offset from the inwardly extending protrusions 184*b* and 185*b*. As a result, the outwardly extending protrusion 180*a* may no longer contact the inwardly extending protrusions 184*a* and 185*a* when the syringe holder 133 is distally moved back into or through the first axial position and the outwardly extending protrusion 180*b* may no longer contact the inwardly extending protrusions 184*b* and 185*b* when the syringe holder 133 is distally moved back into or through the first axial position.

Next, while maintaining the syringe holder 133 in the second rotational position, the syringe holder 133 (including the syringe 120) may be moved in the distal direction to a second axial position within the housing 112, as shown in FIG. 13. As an example, the syringe holder 133 may be moved in the distal direction until the distally directed end surface 175 of the syringe holder 133 comes into contact with and/or abuts against the proximally directed surface 186*a* of the inwardly extending protrusion 186 of the housing 112. Further distal movement of the syringe holder 133 with respect to the housing 112 may be prevented as a result of this contact. When in the second axial position, the syringe holder 133 may be said to be seated within the housing 112 and/or in its final assembled position. In some embodiments, moving the syringe holder 133 into the second axial position may result in the removable sterile barrier 121 being inserted into and/or gripped by a gripper (e.g., the gripper 13 described above) arranged inside of the removable cap 119.

Moving the syringe holder 133 in the distal direction from the first axial position to the second axial position may involve applying a distally directed force to the proximal end 166 of the syringe holder 166. As an example, the distally directed force may be applied directly to axially extending arms 190 and 191 located at the proximal end 166 of the syringe holder 166. The distally directed force may not be applied directly to the syringe 120 to avoid moving the syringe 120 in the distal direction with respect to the syringe holder 133, which may be possible prior to arranging the syringe holder 133 in the second axial position because, as mentioned above, the radially inwardly facing surface of the housing 112 may not prevent the axially extending arms 176*a* and 176*b* of the syringe holder 133 from flexing radially outwardly until the syringe holder 133 is in the second axial position.

Subsequent to positioning the syringe holder 133 in the second axial position, other components may be assembled into the housing 112. For example, a drive mechanism (e.g., the drive mechanism 30 described above) may be positioned within the housing 112 at least partially proximal to the syringe holder 133. Once all of the necessary components and/or mechanisms have been assembled into the housing 112, the axial opening 164 in the proximal end 162 of the housing 112 may be closed off with an end cap (e.g., the end cap 23 described above).

Referring now to FIGS. 16-19, another embodiment of a syringe holder (designated as syringe holder 233) will be described. The syringe holder 233 includes elements that are similar or identical in structure, configuration, and/or function to elements of the syringe holder 133 described above in conjunction with FIGS. 3-15. Such components are assigned with the same reference numeral as used in FIGS. 3-15, except incremented by 100. A description of certain of these components is abbreviated or eliminated in the interest of conciseness.

Figures 18, 19:
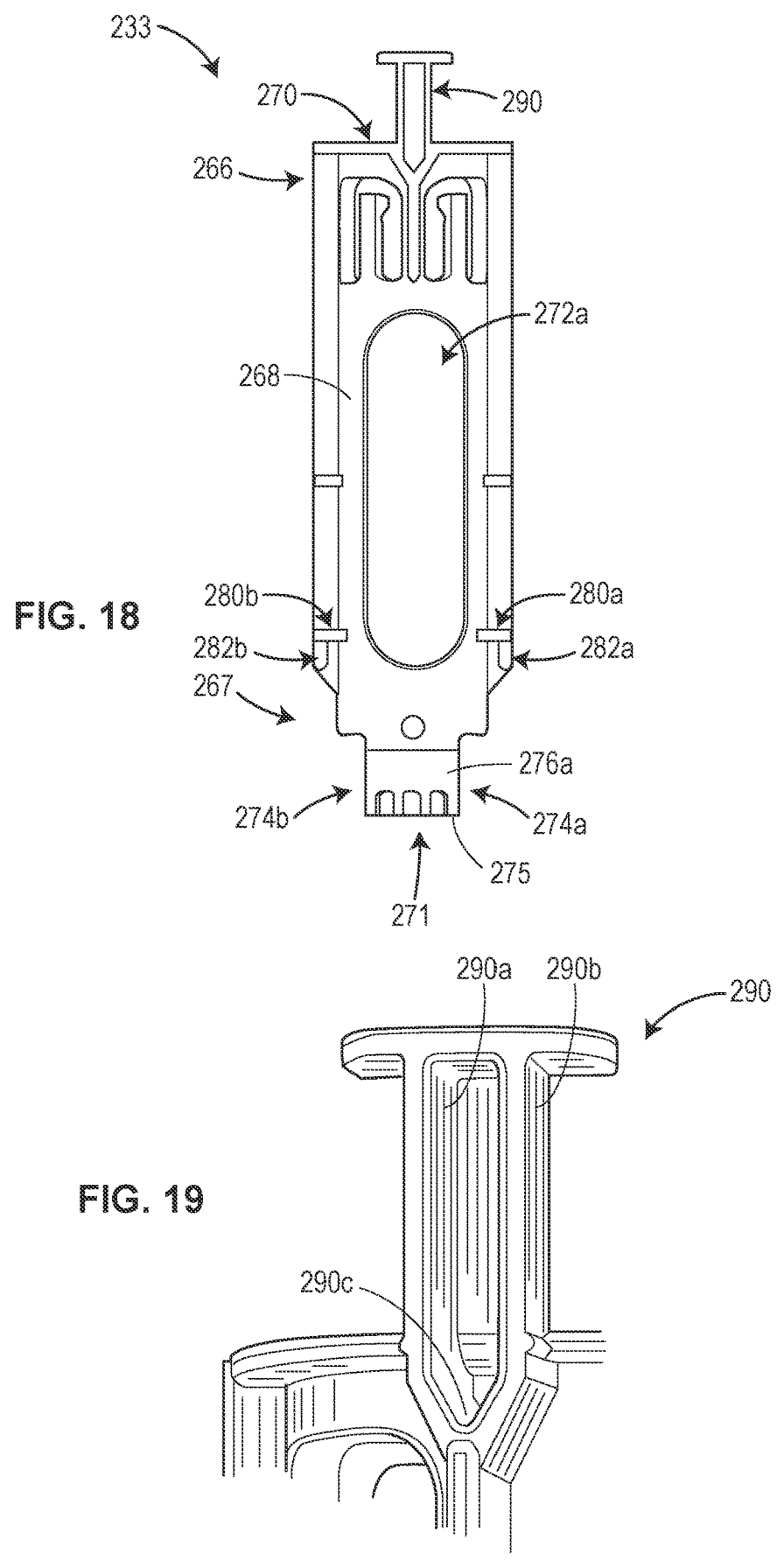

As illustrated in FIGS. 16 and 19, the proximal end 266 of the syringe holder 233 may include an axially extending protrusion 290 and an axially extending protrusion 291. As an example, the axially extending protrusion 290 includes an inwardly facing surface 290a and an outwardly facing surface 290b, as depicted in FIG. 19. As a more specific example, the inwardly facing surface 290a includes at least one rounded corner 290c adjacent the distal end of the axially extending protrusion 290. As an even more specific example, the inwardly facing surface 290a and the outwardly facing surface 290b each possesses a respective draft. The axially extending protrusion 291 may be arranged across the longitudinal axis of the syringe holder 233 from the axially extending protrusion 291 and may be configured in a similar manner as the axially extending protrusion 290.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-?4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF? monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRASG12C small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
a housing having a proximal end, a distal end, an opening formed in the distal end, and a longitudinal axis;
a syringe including a reservoir configured to contain a drug and a needle configured to be in fluid communication with the reservoir, the needle having an insertion end configured to extend at least partially through the opening during a delivery state; and
a syringe holder comprising:
a proximal end and a distal end,
a hollow interior configured to receive at least a portion of the syringe,
a side opening formed below the proximal end of the syringe holder, and
an outwardly extending protrusion,
wherein, during assembly of the syringe holder into the housing, the outwardly extending protrusion is configured to contact a first inner portion of the housing to support the syringe holder at a first axial position with respect to the longitudinal axis of the housing and prevent the syringe holder from moving in a distal direction with respect to the housing at least during insertion of the syringe into the syringe holder, and
wherein at least a portion of the syringe holder is configured to contact a second inner portion of the housing when the syringe holder is in a second axial position with respect to the longitudinal axis of the housing to prevent the syringe holder from moving in the distal direction with respect to the housing, the second axial position being below the first axial position with respect to the longitudinal axis of the housing.

2. The drug delivery device of claim 1, wherein the outwardly extending protrusion is configured to contact the first inner portion of the housing when the syringe holder is in a first rotational position with respect to the housing to prevent the syringe holder from moving in the distal direction with respect to the housing.

3. The drug delivery device of claim 2, wherein the outwardly extending protrusion is (a) configured to permit movement of the syringe holder in a proximal direction with respect to the housing when the syringe holder is in the first axial position, and/or (b) configured such that the outwardly extending protrusion is rotationally offset from the first inner portion of the housing when the syringe holder is in a second rotational position with respect to the housing to permit movement of the syringe holder in the distal direction with respect to the housing.

4. The drug delivery device of claim 1, wherein the at least a portion of the syringe holder comprises a distally directed surface of the distal end of the syringe holder.

5. The drug delivery device of claim 1, wherein the syringe holder comprises a second outwardly extending protrusion disposed below the outwardly extending protrusion, wherein at least one of the outwardly extending protrusion and the second outwardly extending protrusion contacts an inner portion of the housing when the syringe holder is in the first axial position to prevent the syringe holder from rotating in at least one rotational direction with respect to the housing.

6. The drug delivery device of claim 5, wherein the second outwardly extending protrusion is configured to be received between two inwardly extending protrusions of the housing when the syringe holder is in the first axial position to prevent the syringe holder from rotating with respect to the housing, wherein the second outwardly extending protrusion is configured to form an interference-fit with the two inwardly extending protrusions of the housing.

7. The drug delivery device of claim 1, wherein at least a portion of the side opening is configured to align with at least a portion of a side opening of the housing when the syringe holder is in the first axial position.

8. A syringe holder for a drug delivery device, the syringe holder comprising:

a proximal end and a distal end;

a hollow interior configured to receive at least a portion of a syringe, the syringe including a reservoir configured to contain a drug and a needle configured to be in fluid communication with the reservoir;

a side opening formed below the proximal end; and an outwardly extending protrusion, wherein, during assembly of the syringe holder into a housing of the drug delivery device, the outwardly extending protrusion is configured to contact a first inner portion of the housing of the drug delivery device to support the syringe holder at a first axial position with respect to a longitudinal axis of the housing of the drug delivery device and prevent the syringe holder from moving in a distal direction with respect to the housing at least during insertion of the syringe into the syringe holder, and wherein at least a portion of the syringe holder is configured to contact a second inner portion of the housing when the syringe holder is in a second axial position with respect to the longitudinal axis of the housing of the drug delivery device to prevent the syringe holder from moving in the distal direction with respect to the housing of the drug delivery device, the second axial position being below the first axial position with respect to the longitudinal axis of the housing.

9. The syringe holder of claim 8, wherein the outwardly extending protrusion is configured to contact the first inner portion of the housing of the drug delivery device when the syringe holder is in a first rotational position with respect to the housing of the drug delivery device to prevent the syringe holder from moving in the distal direction with respect to the housing of the drug delivery device.

10. The syringe holder of claim 9, wherein the outwardly extending protrusion is (a) configured to permit movement of the syringe holder in a proximal direction with respect to the housing of the drug delivery device when the syringe holder is in the first axial position and/or (b) configured such that the outwardly extending protrusion is rotationally offset from the first inner portion of the housing of the drug delivery device when the syringe holder is in a second rotational position with respect to the housing of the drug delivery device to permit movement of the syringe holder in the distal direction with respect to the housing of the drug delivery device.

11. The syringe holder of claim 8, wherein the at least a portion of the syringe holder comprises a distally directed surface of the distal end of the syringe holder.

12. The syringe holder of claim 8, wherein the syringe holder comprises a second outwardly extending protrusion disposed below the outwardly extending protrusion, wherein at least one of the outwardly extending protrusion and the second outwardly extending protrusion contacts an inner portion of the housing of the drug delivery device when the syringe holder is in the first axial position to prevent the syringe holder from rotating in at least one rotational direction with respect to the housing of the drug delivery device.

13. The syringe holder of claim 12, wherein the second outwardly extending protrusion is configured to be received between two inwardly extending protrusions of the housing of the drug delivery device when the syringe holder is in the first axial position to prevent the syringe holder from rotating with respect to the housing of the drug delivery device, wherein the second outwardly extending protrusion is configured to form an interference-fit with the two inwardly extending protrusions of the housing of the drug delivery device.

14. The syringe holder of claim 8, wherein at least a portion of the side opening is configured to align with at least a portion of a side opening of the housing of the drug delivery device when the syringe holder is in the first axial position.

15. A subassembly for a drug delivery device, the subassembly comprising:

a syringe holder comprising an outwardly extending protrusion and configured to receive at least a portion of a syringe, the syringe including a reservoir configured to contain a drug and a needle configured to be in fluid communication with the reservoir;

a housing comprising:

a hollow interior configured to receive at least a portion of the syringe holder, a first inwardly extending protrusion, and a second inwardly extending protrusion disposed below distal to the first inwardly extending protrusion; and wherein, during assembly, the syringe holder is in a first axial position with respect to a longitudinal axis of the housing where the outwardly extending protrusion of the syringe holder contacts the first inwardly extending protrusion of the housing to prevent the syringe holder from moving in a distal direction with respect to the housing at least during insertion of the syringe into the syringe holder and, subsequently, a second axial position with respect to the longitudinal axis of the housing where at least a portion of the syringe holder contacts the second inwardly extending protrusion of the housing, the second axial position being below the first axial position with respect to the longitudinal axis of the housing.

16. The subassembly of claim 15, wherein the first inwardly extending protrusion is configured to prevent the syringe holder from moving in a distal direction with respect to the housing when the syringe holder is in a first rotational position with respect to the housing.

17. The subassembly of claim 16, wherein the first inwardly extending protrusion is configured to permit the syringe holder to move in the distal direction with respect to the housing when the syringe holder is in a second rotational position with respect to the housing, wherein the syringe holder is in the second rotational position when the syringe holder is in the second axial position.

18. The subassembly of claim 15, wherein the syringe holder comprises a second outwardly extending protrusion disposed below the outwardly extending protrusion, wherein at least one of the outwardly extending protrusion and the second outwardly extending protrusion contacts the first inwardly extending protrusion when the syringe holder is in the first axial position to prevent the syringe holder from rotating in at least one rotational direction with respect to the housing.

19. The subassembly of claim 18, wherein the housing comprises a third inwardly extending protrusion adjacent to the first inwardly extending protrusion, and wherein the second outwardly extending protrusion of the syringe holder is disposed between the first inwardly extending protrusion of the housing and the third inwardly extending protrusion of the housing when the syringe holder is in the first axial position to prevent the syringe holder from rotating with respect to the housing, wherein an interference-fit is formed between the second outwardly extending protrusion of the syringe holder and the first and third inwardly extending protrusions of the housing when the syringe holder is in the first axial position.

20. The subassembly of claim 15, wherein the syringe holder has a side opening, wherein the housing has a side opening distal to the first inwardly extending protrusion of the housing, wherein at least a portion of the side opening of the syringe holder is configured to align with at least a portion of the side opening of the housing when the syringe holder is in the first axial position and/or a first rotational position.

* * * * *